(12) United States Patent
Khrestchatisky et al.

(10) Patent No.: US 9,328,143 B2
(45) Date of Patent: *May 3, 2016

(54) PEPTIDE DERIVATIVES AND USE THEREOF AS CARRIERS FOR MOLECULES IN THE FORM OF CONJUGATES

(71) Applicants: VECT-HORUS, Marseilles (FR); CENTRE NATIONAL DE LA RECHERCHE SCIENTIFIQUE, Paris (FR); UNIVERSITE D'AIX MARSEILLE, Marseilles (FR)

(72) Inventors: Michel Khrestchatisky, Marseilles (FR); Marion David, Marsielles (FR); Yves Molino, Carry le Rouet (FR); Patrick Vlieghe, Bandol (FR)

(73) Assignees: VECT-HORUS, Marseilles (FR); CENTRE NATIONAL DE LA RECHERCHE SCIENTIFIQUE, Paris (FR); UNIVERSITE DE LA MEDITERRANEE (AIX MARSEILLE II), Marseilles (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/277,339

(22) Filed: May 14, 2014

(65) Prior Publication Data

US 2014/0243499 A1 Aug. 28, 2014

Related U.S. Application Data

(63) Continuation of application No. 13/125,634, filed as application No. PCT/FR2009/051991 on Oct. 20, 2009, now Pat. No. 8,729,029.

(30) Foreign Application Priority Data

Oct. 22, 2008 (FR) ...................................... 08 57159

(51) Int. Cl.
| | |
|---|---|
| *C07K 7/64* | (2006.01) |
| *A61K 38/12* | (2006.01) |
| *C07K 7/08* | (2006.01) |
| *C07K 14/775* | (2006.01) |
| *C07K 4/00* | (2006.01) |
| *C07K 7/06* | (2006.01) |
| *C07K 14/00* | (2006.01) |
| *A61K 38/00* | (2006.01) |

(52) U.S. Cl.
CPC ... *C07K 7/64* (2013.01); *C07K 4/00* (2013.01); *C07K 7/06* (2013.01); *C07K 7/08* (2013.01); *C07K 14/00* (2013.01); *C07K 14/775* (2013.01); *A61K 38/00* (2013.01)

(58) Field of Classification Search
CPC ........ A61K 38/00; C07K 7/08; C07K 14/775; C07K 14/00; C07K 7/06; C07K 7/64; C07K 4/00

See application file for complete search history.

(56) References Cited

U.S. PATENT DOCUMENTS

| | | | |
|---|---|---|---|
| 2004/0123343 A1 | 6/2004 | La Rosa et al. | |
| 2005/0058603 A1* | 3/2005 | Gao ..................... | A61K 9/5089 424/9.32 |
| 2006/0135434 A1* | 6/2006 | Kulseth ........................... | 514/15 |
| 2011/0230416 A1 | 9/2011 | Khrestchatisky et al. | |
| 2013/0108548 A1 | 5/2013 | Vlieghe et al. | |

FOREIGN PATENT DOCUMENTS

| | | |
|---|---|---|
| CA | 2 796 174 | 10/2011 |
| WO | WO 99/47566 | 9/1999 |
| WO | WO 01/81581 | 11/2001 |
| WO | WO 2004/108071 | 12/2004 |
| WO | WO 2010/046588 | 4/2010 |
| WO | WO 2011/131896 | 10/2011 |

OTHER PUBLICATIONS

Sugase et al, Structure—Activity Relationships for Mini Atrial Natriuretic Peptide by Proline-Scanning Mutagenesis and Shortening of Peptide Backbone, Bioorganic & Medicinal Chemistry Letters, 2002, 12, pp. 1245-1247.*
Adessi et al, Converting a Peptide into a Drug: Strategies to Improve Stability and Bioavailability, Current Medicinal Chemistry, 2002, 9, pp. 963-978.*
Leader et al, Protein therapeutics: a summary and pharmacological classification, Nature Reviews, 2008, 7, pp. 21-39.*
Blast search of peptide CMPRC, from http://blast.ncbi.nlm.nih.gov/Blast.cgi, pp. 1-27, accessed May 11, 2015.*
Joo, Cyclic Peptides as Therapeutic Agents and Biochemical Tools, Biomol Ther, 2012, 20, pp. 19-26.*
Voet, D. et al. Biochemistry Second Edition, *John Wiley & Sons, Inc.*, 1995, pp. 235-241.
Definitions of analog and analogue, from http://cancerweb.ncl.ac.uk/cgi-bin/omd?query=analog, pp. 1-5, accessed Jul. 7, 2005.
Ngo, J. Thomas et al. "Computational Complexity, Protein Structure Prediction, and the Levinthal Paradox" *The Protein Folding Problem and Tertiary Structure Prediction*,1994, pp. 491-494.
Rudinger, J. "Characteristics of the amino acids as components of a peptide hormone sequence" *Peptide Hormones*, Jun. 1976, pp. 1-7.

(Continued)

*Primary Examiner* — Julie Ha
*Assistant Examiner* — Li Ni Komatsu
(74) *Attorney, Agent, or Firm* — Saliwanchik, Lloyd & Eisenschenk

(57) ABSTRACT

The invention relates to peptide derivatives (peptides and pseudo-peptides) and use thereof as vectors for molecules of interest. The invention also relates to conjugates containing a peptide derivative of the invention bound to a molecule of interest. The peptides and prodrug conjugates of the invention can be used to vectorize molecules of pharmaceutical or diagnostic interest, such as, for example, therapeutic molecules, imaging or diagnostic agents, or molecular probes, across cell membranes, and notably to promote their transport across the blood-brain barrier (BBB).

14 Claims, 16 Drawing Sheets
(4 of 16 Drawing Sheet(s) Filed in Color)

(56) References Cited

OTHER PUBLICATIONS

Bradley, Christina et al. "Limits of Cooperativity in a Structurally Modular Protein: Response of the Notch Ankyrin Domain to Analogous Alanine Substitutions in Each Repeat" *J. Mol. Biol.*, 2002, pp. 373-386, vol. 324.

Berendsen, Herman J.C. "A Glimpse of the Holy Grail?" *Science*, Oct. 23, 1998, pp. 642-643, vol. 282.

Sigma, "Designing Custom Peptides" 2004, pp. 1-2.

Itoh, T. et al. "Curated genome annotation of *Oryza sativa* ssp. *japonica* and comparative genome analysis with *Arabidopsis thaliana*" *Genome Research*, Feb. 2007, pp. 175-183, vol. 17, No. 2, XP-002615680.

Database GenBank [Online], "Curated genome annotation of *Oryza sativa* ssp. *japonica* and comparative genome analysis with *Arabidopsis thaliana*" Accession No. BAF08354, pp. 1-3, 2007, XP-002615681.

Sequence ID No. 110851 from US 2004/123343, Jun. 24, 2004, p. 1, XP-002615682.

Sequence ID No. 14215 from WO 2001/81581, Nov. 1, 2001, p. 1, XP-002615683.

\* cited by examiner a). Synthesis in tandem b). Synthesis via a linker

A

B

C

SEQUENCE LISTING

```
<160> NUMBER OF SEQ ID NOS: 78

<210> SEQ ID NO 1
<211> LENGTH: 12
<212> TYPE: PRT
<213> ORGANISM: artificial sequence
<220> FEATURE:
<223> OTHER INFORMATION: synthesized peptide

<400> SEQUENCE: 1

His Leu Asp Cys Met Pro Arg Gly Cys Phe Arg Asn
1               5                   10

<210> SEQ ID NO 2
<211> LENGTH: 10
<212> TYPE: PRT
<213> ORGANISM: artificial sequence
<220> FEATURE:
<223> OTHER INFORMATION: synthesized peptide

<400> SEQUENCE: 2
```

```
Ala Cys Gln Val Lys Ser Met Pro Arg Cys
1               5                   10

<210> SEQ ID NO 3
<211> LENGTH: 10
<212> TYPE: PRT
<213> ORGANISM: artificial sequence
<220> FEATURE:
<223> OTHER INFORMATION: synthesized peptide

<400> SEQUENCE: 3

Ala Cys Thr Thr Pro Met Pro Arg Leu Cys
1               5                   10

<210> SEQ ID NO 4
<211> LENGTH: 10
<212> TYPE: PRT
<213> ORGANISM: artificial sequence
<220> FEATURE:
<223> OTHER INFORMATION: synthesized peptide

<400> SEQUENCE: 4

Ala Cys Lys Ala Pro Gln Met Pro Arg Cys
1               5                   10

<210> SEQ ID NO 5
<211> LENGTH: 10
<212> TYPE: PRT
<213> ORGANISM: artificial sequence
<220> FEATURE:
<223> OTHER INFORMATION: synthesized peptide

<400> SEQUENCE: 5

Ala Cys Leu Asn Pro Ser Met Pro Arg Cys
1               5                   10

<210> SEQ ID NO 6
<211> LENGTH: 10
<212> TYPE: PRT
<213> ORGANISM: artificial sequence
<220> FEATURE:
<223> OTHER INFORMATION: synthesized peptide

<400> SEQUENCE: 6

Ala Cys Leu Val Ser Ser Met Pro Arg Cys
1               5                   10

<210> SEQ ID NO 7
<211> LENGTH: 10
<212> TYPE: PRT
<213> ORGANISM: artificial sequence
<220> FEATURE:
<223> OTHER INFORMATION: synthesized peptide

<400> SEQUENCE: 7

Ala Cys Leu Gln Pro Met Pro Arg Leu Cys
1               5                   10

<210> SEQ ID NO 8
<211> LENGTH: 10
<212> TYPE: PRT
<213> ORGANISM: artificial sequence
<220> FEATURE:
<223> OTHER INFORMATION: synthesized peptide

<400> SEQUENCE: 8

Ala Cys Pro Val Ser Ser Met Pro Arg Cys
```

```
1               5                   10
```

<210> SEQ ID NO 9
<211> LENGTH: 10
<212> TYPE: PRT
<213> ORGANISM: artificial sequence
<220> FEATURE:
<223> OTHER INFORMATION: synthesized peptide

<400> SEQUENCE: 9

```
Ala Cys Gln Ser Pro Met Pro Arg Leu Cys
1               5                   10
```

<210> SEQ ID NO 10
<211> LENGTH: 10
<212> TYPE: PRT
<213> ORGANISM: artificial sequence
<220> FEATURE:
<223> OTHER INFORMATION: synthesized peptide

<400> SEQUENCE: 10

```
Ala Cys Leu Thr Pro Met Pro Arg Leu Cys
1               5                   10
```

<210> SEQ ID NO 11
<211> LENGTH: 15
<212> TYPE: PRT
<213> ORGANISM: artificial sequence
<220> FEATURE:
<223> OTHER INFORMATION: synthesized peptide

<400> SEQUENCE: 11

```
Asp Ser Gly Leu Cys Met Pro Arg Leu Arg Gly Cys Asp Pro Arg
1               5                   10                  15
```

<210> SEQ ID NO 12
<211> LENGTH: 15
<212> TYPE: PRT
<213> ORGANISM: artificial sequence
<220> FEATURE:
<223> OTHER INFORMATION: synthesized peptide

<400> SEQUENCE: 12

```
Met Thr Val Met Pro Thr Gly Leu Trp Asn Pro Leu Ile Pro Ser
1               5                   10                  15
```

<210> SEQ ID NO 13
<211> LENGTH: 15
<212> TYPE: PRT
<213> ORGANISM: artificial sequence
<220> FEATURE:
<223> OTHER INFORMATION: synthesized peptide

<400> SEQUENCE: 13

```
Ser Ala Ser Trp Phe Ala Val Pro Ile Pro Pro Leu Arg Leu Glu
1               5                   10                  15
```

<210> SEQ ID NO 14
<211> LENGTH: 15
<212> TYPE: PRT
<213> ORGANISM: artificial sequence
<220> FEATURE:
<223> OTHER INFORMATION: synthesized peptide

<400> SEQUENCE: 14

```
Met Thr Pro Met Ser Thr Pro Arg Met Leu Pro Val Tyr Val Ala
1               5                   10                  15
```

```
<210> SEQ ID NO 15
<211> LENGTH: 15
<212> TYPE: PRT
<213> ORGANISM: artificial sequence
<220> FEATURE:
<223> OTHER INFORMATION: synthesized peptide

<400> SEQUENCE: 15

Met Thr Ala Thr His Leu Ser Thr Leu Phe Gln Pro Leu Thr Tyr
1               5                   10                  15

<210> SEQ ID NO 16
<211> LENGTH: 15
<212> TYPE: PRT
<213> ORGANISM: artificial sequence
<220> FEATURE:
<223> OTHER INFORMATION: synthesized peptide

<400> SEQUENCE: 16

Met Ser Pro Ile Pro Pro Ala Ala Ser Thr Trp Ala Asn Thr Leu
1               5                   10                  15

<210> SEQ ID NO 17
<211> LENGTH: 15
<212> TYPE: PRT
<213> ORGANISM: artificial sequence
<220> FEATURE:
<223> OTHER INFORMATION: synthesized peptide

<400> SEQUENCE: 17

Met Thr Ala Asn Pro Leu Gln Asn Ala Pro Gly Pro Leu Ser Leu
1               5                   10                  15

<210> SEQ ID NO 18
<211> LENGTH: 15
<212> TYPE: PRT
<213> ORGANISM: artificial sequence
<220> FEATURE:
<223> OTHER INFORMATION: synthesized peptide

<400> SEQUENCE: 18

Met Gln Thr Ala Pro Pro Pro Pro Leu Thr Arg Val Gln Trp Ser
1               5                   10                  15

<210> SEQ ID NO 19
<211> LENGTH: 15
<212> TYPE: PRT
<213> ORGANISM: artificial sequence
<220> FEATURE:
<223> OTHER INFORMATION: synthesized peptide

<400> SEQUENCE: 19

Gly Thr Pro Arg Met His Ile Pro Leu Asn Val Asp His Leu Pro
1               5                   10                  15

<210> SEQ ID NO 20
<211> LENGTH: 15
<212> TYPE: PRT
<213> ORGANISM: artificial sequence
<220> FEATURE:
<223> OTHER INFORMATION: synthesized peptide

<400> SEQUENCE: 20

Leu Thr Leu Pro Pro Ile Ser Gly Leu Ser Ser Tyr Pro Leu Pro
1               5                   10                  15
```

```
<210> SEQ ID NO 21
<211> LENGTH: 15
<212> TYPE: PRT
<213> ORGANISM: artificial sequence
<220> FEATURE:
<223> OTHER INFORMATION: synthesized peptide

<400> SEQUENCE: 21

Thr Pro Ser Ala His Ala Met Ala Leu Gln Ser Leu Ser Val Gly
1               5                   10                  15

<210> SEQ ID NO 22
<211> LENGTH: 15
<212> TYPE: PRT
<213> ORGANISM: artificial sequence
<220> FEATURE:
<223> OTHER INFORMATION: synthesized peptide

<400> SEQUENCE: 22

Leu Thr Leu Pro Pro Ile Ser Gly Leu Ser Ser Tyr Pro Leu Pro
1               5                   10                  15

<210> SEQ ID NO 23
<211> LENGTH: 15
<212> TYPE: PRT
<213> ORGANISM: artificial sequence
<220> FEATURE:
<223> OTHER INFORMATION: synthesized peptide

<400> SEQUENCE: 23

Met Gly Thr Leu Asn Ala Pro Thr Ala Tyr Pro Gln Asp Ser Leu
1               5                   10                  15

<210> SEQ ID NO 24
<211> LENGTH: 15
<212> TYPE: PRT
<213> ORGANISM: artificial sequence
<220> FEATURE:
<223> OTHER INFORMATION: synthesized peptide

<400> SEQUENCE: 24

Leu Thr Asn Pro Pro Ala Tyr Leu Pro Gln Asn Thr Asp Pro His
1               5                   10                  15

<210> SEQ ID NO 25
<211> LENGTH: 15
<212> TYPE: PRT
<213> ORGANISM: artificial sequence
<220> FEATURE:
<223> OTHER INFORMATION: synthesized peptide

<400> SEQUENCE: 25

Met Gly Leu Pro Leu Pro Tyr Ile Gln Thr Ile Leu His Thr Pro
1               5                   10                  15

<210> SEQ ID NO 26
<211> LENGTH: 15
<212> TYPE: PRT
<213> ORGANISM: artificial sequence
<220> FEATURE:
<223> OTHER INFORMATION: synthesized peptide

<400> SEQUENCE: 26

Ser Ala Ala Leu Ile Ala Met Ser Ser Phe Lys Ser Ile Thr Ala
1               5                   10                  15
```

```
<210> SEQ ID NO 27
<211> LENGTH: 15
<212> TYPE: PRT
<213> ORGANISM: artificial sequence
<220> FEATURE:
<223> OTHER INFORMATION: synthesized peptide

<400> SEQUENCE: 27

Ser Gly Phe Ala Phe Ala Arg Ser Val Pro Thr Glu Ser Arg Arg
1               5                   10                  15

<210> SEQ ID NO 28
<211> LENGTH: 15
<212> TYPE: PRT
<213> ORGANISM: artificial sequence
<220> FEATURE:
<223> OTHER INFORMATION: synthesized peptide

<400> SEQUENCE: 28

Met Thr Ser Pro Tyr Met Ser Leu Pro Pro Ser Thr Asp Asp Met
1               5                   10                  15

<210> SEQ ID NO 29
<211> LENGTH: 15
<212> TYPE: PRT
<213> ORGANISM: artificial sequence
<220> FEATURE:
<223> OTHER INFORMATION: synthesized peptide

<400> SEQUENCE: 29

Leu Thr Asn Pro Pro Ala Tyr Leu Pro Gln Asn Thr Asp Pro His
1               5                   10                  15

<210> SEQ ID NO 30
<211> LENGTH: 10
<212> TYPE: PRT
<213> ORGANISM: artificial sequence
<220> FEATURE:
<223> OTHER INFORMATION: synthesized peptide

<400> SEQUENCE: 30

Ala Cys Met Pro Arg Leu Arg Gly Cys Ala
1               5                   10

<210> SEQ ID NO 31
<211> LENGTH: 15
<212> TYPE: PRT
<213> ORGANISM: artificial sequence
<220> FEATURE:
<223> OTHER INFORMATION: synthesized peptide

<400> SEQUENCE: 31

Ala Ser Gly Leu Cys Met Pro Arg Leu Arg Gly Cys Asp Pro Arg
1               5                   10                  15

<210> SEQ ID NO 32
<211> LENGTH: 15
<212> TYPE: PRT
<213> ORGANISM: artificial sequence
<220> FEATURE:
<223> OTHER INFORMATION: synthesized peptide

<400> SEQUENCE: 32

Asp Ala Gly Leu Cys Met Pro Arg Leu Arg Gly Cys Asp Pro Arg
1               5                   10                  15

<210> SEQ ID NO 33
```

```
<211> LENGTH: 15
<212> TYPE: PRT
<213> ORGANISM: artificial sequence
<220> FEATURE:
<223> OTHER INFORMATION: synthesized peptide

<400> SEQUENCE: 33

Asp Ser Ala Leu Cys Met Pro Arg Leu Arg Gly Cys Asp Pro Arg
1               5                   10                  15

<210> SEQ ID NO 34
<211> LENGTH: 15
<212> TYPE: PRT
<213> ORGANISM: artificial sequence
<220> FEATURE:
<223> OTHER INFORMATION: synthesized peptide

<400> SEQUENCE: 34

Asp Ser Gly Ala Cys Met Pro Arg Leu Arg Gly Cys Asp Pro Arg
1               5                   10                  15

<210> SEQ ID NO 35
<211> LENGTH: 15
<212> TYPE: PRT
<213> ORGANISM: artificial sequence
<220> FEATURE:
<223> OTHER INFORMATION: synthesized peptide

<400> SEQUENCE: 35

Asp Ser Gly Leu Cys Met Pro Arg Ala Arg Gly Cys Asp Pro Arg
1               5                   10                  15

<210> SEQ ID NO 36
<211> LENGTH: 15
<212> TYPE: PRT
<213> ORGANISM: artificial sequence
<220> FEATURE:
<223> OTHER INFORMATION: synthesized peptide

<400> SEQUENCE: 36

Asp Ser Gly Leu Cys Met Pro Arg Leu Ala Gly Cys Asp Pro Arg
1               5                   10                  15

<210> SEQ ID NO 37
<211> LENGTH: 15
<212> TYPE: PRT
<213> ORGANISM: artificial sequence
<220> FEATURE:
<223> OTHER INFORMATION: synthesized peptide

<400> SEQUENCE: 37

Asp Ser Gly Leu Cys Met Pro Arg Leu Arg Ala Cys Asp Pro Arg
1               5                   10                  15

<210> SEQ ID NO 38
<211> LENGTH: 15
<212> TYPE: PRT
<213> ORGANISM: artificial sequence
<220> FEATURE:
<223> OTHER INFORMATION: synthesized peptide

<400> SEQUENCE: 38

Asp Ser Gly Leu Cys Met Pro Arg Leu Arg Gly Cys Ala Pro Arg
1               5                   10                  15

<210> SEQ ID NO 39
<211> LENGTH: 15
```

```
<212> TYPE: PRT
<213> ORGANISM: artificial sequence
<220> FEATURE:
<223> OTHER INFORMATION: synthesized peptide

<400> SEQUENCE: 39

Asp Ser Gly Leu Cys Met Pro Arg Leu Arg Gly Cys Asp Ala Arg
1               5                   10                  15

<210> SEQ ID NO 40
<211> LENGTH: 15
<212> TYPE: PRT
<213> ORGANISM: artificial sequence
<220> FEATURE:
<223> OTHER INFORMATION: synthesized peptide

<400> SEQUENCE: 40

Asp Ser Gly Leu Cys Met Pro Arg Leu Arg Gly Cys Asp Pro Ala
1               5                   10                  15

<210> SEQ ID NO 41
<211> LENGTH: 14
<212> TYPE: PRT
<213> ORGANISM: artificial sequence
<220> FEATURE:
<223> OTHER INFORMATION: synthesized peptide

<400> SEQUENCE: 41

Ser Gly Leu Cys Met Pro Arg Leu Arg Gly Cys Asp Pro Arg
1               5                   10

<210> SEQ ID NO 42
<211> LENGTH: 13
<212> TYPE: PRT
<213> ORGANISM: artificial sequence
<220> FEATURE:
<223> OTHER INFORMATION: synthesized peptide

<400> SEQUENCE: 42

Gly Leu Cys Met Pro Arg Leu Arg Gly Cys Asp Pro Arg
1               5                   10

<210> SEQ ID NO 43
<211> LENGTH: 8
<212> TYPE: PRT
<213> ORGANISM: artificial sequence
<220> FEATURE:
<223> OTHER INFORMATION: synthesized peptide

<400> SEQUENCE: 43

Cys Met Pro Arg Leu Arg Gly Cys
1               5

<210> SEQ ID NO 44
<211> LENGTH: 8
<212> TYPE: PRT
<213> ORGANISM: artificial sequence
<220> FEATURE:
<223> OTHER INFORMATION: synthesized peptide

<400> SEQUENCE: 44

Cys Met Pro Arg Ala Arg Gly Cys
1               5

<210> SEQ ID NO 45
<211> LENGTH: 8
<212> TYPE: PRT
```

```
<213> ORGANISM: artificial sequence
<220> FEATURE:
<223> OTHER INFORMATION: synthesized peptide

<400> SEQUENCE: 45

Cys Met Pro Arg Leu Ala Gly Cys
1               5

<210> SEQ ID NO 46
<211> LENGTH: 8
<212> TYPE: PRT
<213> ORGANISM: artificial sequence
<220> FEATURE:
<223> OTHER INFORMATION: synthesized peptide

<400> SEQUENCE: 46

Cys Met Pro Arg Leu Arg Ala Cys
1               5

<210> SEQ ID NO 47
<211> LENGTH: 8
<212> TYPE: PRT
<213> ORGANISM: artificial sequence
<220> FEATURE:
<223> OTHER INFORMATION: synthesized peptide

<400> SEQUENCE: 47

Cys Met Pro Arg Leu Lys Gly Cys
1               5

<210> SEQ ID NO 48
<211> LENGTH: 8
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (1)..(1)
<223> OTHER INFORMATION: Xaa = (D)-Cystein

<400> SEQUENCE: 48

Xaa Met Pro Arg Leu Arg Gly Cys
1               5

<210> SEQ ID NO 49
<211> LENGTH: 8
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (5)..(5)
<223> OTHER INFORMATION: Xaa = (D)-Leucin

<400> SEQUENCE: 49

Cys Met Pro Arg Xaa Arg Gly Cys
1               5

<210> SEQ ID NO 50
<211> LENGTH: 8
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (6)..(6)
```

```
<223> OTHER INFORMATION: Xaa = (D)-Arginin

<400> SEQUENCE: 50

Cys Met Pro Arg Leu Xaa Gly Cys
1               5

<210> SEQ ID NO 51
<211> LENGTH: 8
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (8)..(8)
<223> OTHER INFORMATION: Xaa = (D)-Cystein

<400> SEQUENCE: 51

Cys Met Pro Arg Leu Arg Gly Xaa
1               5

<210> SEQ ID NO 52
<211> LENGTH: 8
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (1)..(1)
<223> OTHER INFORMATION: Xaa = (D)-Cystein
<220> FEATURE:
<221> NAME/KEY: MISC_FEATURE
<222> LOCATION: (8)..(8)
<223> OTHER INFORMATION: Xaa = (D)-Cystein

<400> SEQUENCE: 52

Xaa Met Pro Arg Leu Arg Gly Xaa
1               5

<210> SEQ ID NO 53
<211> LENGTH: 8
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (1)..(1)
<223> OTHER INFORMATION: Xaa = (D)-Cystein
<220> FEATURE:
<221> NAME/KEY: MISC_FEATURE
<222> LOCATION: (7)..(7)
<223> OTHER INFORMATION: Xaa = Sar

<400> SEQUENCE: 53

Xaa Met Pro Arg Leu Arg Xaa Cys
1               5

<210> SEQ ID NO 54
<211> LENGTH: 8
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (1)..(1)
<223> OTHER INFORMATION: Xaa = (D)-Cystein

<400> SEQUENCE: 54
```

```
Xaa Met Pro Arg Lys Arg Gly Cys
1               5

<210> SEQ ID NO 55
<211> LENGTH: 8
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (1)..(1)
<223> OTHER INFORMATION: Xaa = (D)-Cystein

<400> SEQUENCE: 55

Xaa Met Pro Arg Leu Arg Cys Gly
1               5

<210> SEQ ID NO 56
<211> LENGTH: 8
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (1)..(1)
<223> OTHER INFORMATION: Xaa = (D)-Cystein

<400> SEQUENCE: 56

Xaa Met Pro Arg Leu Cys Arg Gly
1               5

<210> SEQ ID NO 57
<211> LENGTH: 8
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (1)..(1)
<223> OTHER INFORMATION: Xaa = (D)-Cystein

<400> SEQUENCE: 57

Xaa Met Pro Arg Cys Leu Arg Gly
1               5

<210> SEQ ID NO 58
<211> LENGTH: 6
<212> TYPE: PRT
<213> ORGANISM: artificial sequence
<220> FEATURE:
<223> OTHER INFORMATION: synthesized peptide

<400> SEQUENCE: 58

Cys Met Pro Arg Gly Cys
1               5

<210> SEQ ID NO 59
<211> LENGTH: 8
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (1)..(1)
<223> OTHER INFORMATION: Xaa = Pen
```

<400> SEQUENCE: 59

Xaa Met Pro Arg Leu Arg Gly Cys
1               5

<210> SEQ ID NO 60
<211> LENGTH: 8
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (1)..(1)
<223> OTHER INFORMATION: Xaa = (D)-Pen

<400> SEQUENCE: 60

Xaa Met Pro Arg Leu Arg Gly Cys
1               5

<210> SEQ ID NO 61
<211> LENGTH: 8
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (1)..(1)
<223> OTHER INFORMATION: Xaa = (D)-Cystein
<220> FEATURE:
<221> NAME/KEY: MISC_FEATURE
<222> LOCATION: (8)..(8)
<223> OTHER INFORMATION: Xaa = Pen

<400> SEQUENCE: 61

Xaa Met Pro Arg Leu Arg Gly Xaa
1               5

<210> SEQ ID NO 62
<211> LENGTH: 8
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (1)..(1)
<223> OTHER INFORMATION: Xaa = Pen
<220> FEATURE:
<221> NAME/KEY: MISC_FEATURE
<222> LOCATION: (8)..(8)
<223> OTHER INFORMATION: Xaa = Pen

<400> SEQUENCE: 62

Xaa Met Pro Arg Leu Arg Gly Xaa
1               5

<210> SEQ ID NO 63
<211> LENGTH: 8
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (1)..(1)
<223> OTHER INFORMATION: Xaa = (D)-Pen
<220> FEATURE:
<221> NAME/KEY: MISC_FEATURE
<222> LOCATION: (8)..(8)

```
<223> OTHER INFORMATION: Xaa = Pen

<400> SEQUENCE: 63

Xaa Met Pro Arg Leu Arg Gly Xaa
1               5

<210> SEQ ID NO 64
<211> LENGTH: 8
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (1)..(1)
<223> OTHER INFORMATION: Xaa = (D)-Pen
<220> FEATURE:
<221> NAME/KEY: MISC_FEATURE
<222> LOCATION: (8)..(8)
<223> OTHER INFORMATION: Xaa = (D)-Pen

<400> SEQUENCE: 64

Xaa Met Pro Arg Leu Arg Gly Xaa
1               5

<210> SEQ ID NO 65
<211> LENGTH: 8
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (1)..(1)
<223> OTHER INFORMATION: Xaa = Mpa

<400> SEQUENCE: 65

Xaa Met Pro Arg Leu Arg Gly Cys
1               5

<210> SEQ ID NO 66
<211> LENGTH: 14
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (2)..(2)
<223> OTHER INFORMATION: Xaa = (D)-Alanin
<220> FEATURE:
<221> NAME/KEY: MISC_FEATURE
<222> LOCATION: (7)..(7)
<223> OTHER INFORMATION: Xaa = (D)-Cystein

<400> SEQUENCE: 66

Tyr Xaa Gly Phe Leu Arg Xaa Met Pro Arg Leu Arg Gly Cys
1               5                   10

<210> SEQ ID NO 67
<211> LENGTH: 17
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (2)..(2)
<223> OTHER INFORMATION: Xaa = D-Alanin
<220> FEATURE:
<221> NAME/KEY: MISC_FEATURE
```

```
<222> LOCATION: (10)..(10)
<223> OTHER INFORMATION: Xaa = D-Cystein

<400> SEQUENCE: 67

Tyr Xaa Gly Phe Leu Arg Gly Gly Xaa Met Pro Arg Leu Arg Gly
1               5                   10                  15

Cys

<210> SEQ ID NO 68
<211> LENGTH: 18
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (2)..(2)
<223> OTHER INFORMATION: Xaa = D-alanin
<220> FEATURE:
<221> NAME/KEY: MISC_FEATURE
<222> LOCATION: (11)..(11)
<223> OTHER INFORMATION: Xaa = D-cystein

<400> SEQUENCE: 68

Tyr Xaa Gly Phe Leu Arg Gly Phe Leu Gly Xaa Met Pro Arg Leu Arg
1               5                   10                  15

Gly Cys

<210> SEQ ID NO 69
<211> LENGTH: 18
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (2)..(2)
<223> OTHER INFORMATION: Xaa = D-alanin
<220> FEATURE:
<221> NAME/KEY: MISC_FEATURE
<222> LOCATION: (11)..(11)
<223> OTHER INFORMATION: Xaa = D-cystein

<400> SEQUENCE: 69

Tyr Xaa Gly Phe Leu Arg Ala Leu Ala Leu Xaa Met Pro Arg Leu Arg
1               5                   10                  15

Gly Cys

<210> SEQ ID NO 70
<211> LENGTH: 15
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (2)..(2)
<223> OTHER INFORMATION: Xaa = D-alanin
<220> FEATURE:
<221> NAME/KEY: MISC_FEATURE
<222> LOCATION: (7)..(7)
<223> OTHER INFORMATION: Ala= beta-alanine
<220> FEATURE:
<221> NAME/KEY: MISC_FEATURE
<222> LOCATION: (8)..(8)
<223> OTHER INFORMATION: Xaa = D-cystein

<400> SEQUENCE: 70

Tyr Xaa Gly Phe Leu Arg Ala Xaa Met Pro Arg Leu Arg Gly Cys
```

```
<210> SEQ ID NO 71
<211> LENGTH: 15
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (2)..(2)
<223> OTHER INFORMATION: Xaa = D-alanin
<220> FEATURE:
<221> NAME/KEY: MISC_FEATURE
<222> LOCATION: (7)..(7)
<223> OTHER INFORMATION: Xaa = Ahx
<220> FEATURE:
<221> NAME/KEY: MISC_FEATURE
<222> LOCATION: (8)..(8)
<223> OTHER INFORMATION: Xaa = D-cystein

<400> SEQUENCE: 71

Tyr Xaa Gly Phe Leu Arg Xaa Xaa Met Pro Arg Leu Arg Gly Cys
1               5                   10                  15

<210> SEQ ID NO 72
<211> LENGTH: 18
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (2)..(2)
<223> OTHER INFORMATION: Xaa = D-alanin
<220> FEATURE:
<221> NAME/KEY: MISC_FEATURE
<222> LOCATION: (11)..(11)
<223> OTHER INFORMATION: Xaa = D-cystein

<400> SEQUENCE: 72

Tyr Xaa Gly Phe Leu Arg Gly Phe Ala Leu Xaa Met Pro Arg Leu Arg
1               5                   10                  15

Gly Cys

<210> SEQ ID NO 73
<211> LENGTH: 5
<212> TYPE: PRT
<213> ORGANISM: artificial sequence
<220> FEATURE:
<223> OTHER INFORMATION: synthesized peptide

<400> SEQUENCE: 73

Cys Met Pro Arg Cys
1               5

<210> SEQ ID NO 74
<211> LENGTH: 6
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (2)..(2)
<223> OTHER INFORMATION: Xaa = D-alanin

<400> SEQUENCE: 74

Tyr Xaa Gly Phe Leu Arg
1               5
```

```
<210> SEQ ID NO 75
<211> LENGTH: 34
<212> TYPE: DNA
<213> ORGANISM: Artificial Sequence
<220> FEATURE:
<223> OTHER INFORMATION: hLDLR forward primer

<400> SEQUENCE: 75
atatataagc ttcgaggaca cagcaggtcg tgat                                  34

<210> SEQ ID NO 76
<211> LENGTH: 35
<212> TYPE: DNA
<213> ORGANISM: Artificial Sequence
<220> FEATURE:
<223> OTHER INFORMATION: hLDLR reverse primer

<400> SEQUENCE: 76
ttaattgtcg accacgccac gtcatcctcc agact                                 35

<210> SEQ ID NO 77
<211> LENGTH: 32
<212> TYPE: DNA
<213> ORGANISM: Artificial Sequence
<220> FEATURE:
<223> OTHER INFORMATION: mLDLR forward primer

<400> SEQUENCE: 77
atatataagc ttgacgcaac gcagaagcta ag                                    32

<210> SEQ ID NO 78
<211> LENGTH: 32
<212> TYPE: DNA
<213> ORGANISM: Artificial Sequence
<220> FEATURE:
<223> OTHER INFORMATION: mLDLR reverse primer

<400> SEQUENCE: 78
ttaattggta ccgttgccac atcgtcctcc ag                                    32
```

PEPTIDE DERIVATIVES AND USE THEREOF AS CARRIERS FOR MOLECULES IN THE FORM OF CONJUGATES

CROSS-REFERENCE TO RELATED APPLICATIONS

This application is continuation of U.S. Ser. No. 13/125,634, filed May 16, 2011, now U.S. Pat. No. 8,729,029, which is the U.S. national stage application of International Patent Application No. PCT/FR2009/051991, filed Oct. 20, 2009.

The Sequence Listing for this application is labeled "SeqList-replace.txt" which was created on Jul. 27, 2015 and is 20 KB. The entire contents of the sequence listing is incorporated herein by reference in its entirety.

The invention relates to peptide derivatives (peptides and pseudo-peptides) and use thereof as vectors for molecules of interest. The invention also relates to conjugates containing a peptide derivative of the invention bound to a molecule of interest. The peptides and prodrug conjugates of the invention can be used to vectorise molecules of pharmaceutical or diagnostic interest, such as, for example, therapeutic molecules, imaging or diagnostic agents, or molecular probes, across cell membranes, and notably to promote their transport across the blood-brain barrier (BBB).

CONTEXT OF THE INVENTION

According to *IMS Health*, the global market for drugs for treating central nervous system (CNS, brain and spinal cord) pathologies was approximately 70 billion dollars in 2007, with nearly 9 billion dollars of this amount representing products arising from drug delivery technologies (Jain, 2008, *Jain PharmaBiotech Report, Drug Delivery in CNS disorders*). Thus, the CNS is today one of the three largest therapeutic areas, along with cardiovascular medicine and oncology. Although the number of people suffering from CNS disorders and pathologies throughout the world is larger than that of people with cardiovascular diseases or cancers, neurology remains an under-developed market. This is explained by the fact that 98% of potential drugs for treating CNS pathologies do not cross the blood-brain barrier or BBB (Pardridge, 2003, *Mol. Interv.*, 3, 90-105).

Indeed, the brain is protected from potentially toxic substances by the presence of two principal physiological barrier systems: the BBB and the blood-cerebrospinal fluid barrier (BCSFB). The BBB is regarded as the principal route for the uptake of plasma ligands. Its surface area is approximately 5000 times larger than that of the BCSFB. The overall length of the constitutive blood vessels of the BBB is approximately 600 km. Each cm$^3$ of cerebral cortex contains the equivalent of 1 km of blood vessels. The total surface area of the BBB is estimated at 20 m$^2$ (De Boer et al., 2007, *Clin. Pharmacokinet.*, 46(7), 553-576). Thus, the cerebral endothelium, which constitutes the BBB, represents a major obstacle to the use of potential drugs against many CNS disorders, but also a large surface of potential exchange between the blood and nervous tissue.

As a general rule, only a few small lipophilic molecules of approximately 450 to 600 Daltons can cross the BBB (only 2% of drug candidates), that is to say, pass from the blood to the brain. The molecular weight and the size of many drug candidates, which show promising results in animal studies for treating CNS disorders, are considerably larger. Thus, most molecules such as therapeutic peptides or proteins are generally excluded from passage/transport from the blood to the brain, because of the low permeability of brain capillary endothelial cells (BCECs) for these drug candidates. The BCECs organised in vessels are surrounded by a basal lamina, astrocyte end-feet, pericytes and microglial and neuronal cells. The tight association of endothelial cells with astrocyte end-feet is responsible for the development and maintenance of properties of BBB impermeability to most molecules, thus ensuring strict and effective control of molecular exchanges between the blood and the brain in order to maintain brain homeostasis. BCECs are closely bound by tight junctions, compared to other endothelial cells of other organs, which are fenestrated. These tight junctions thus prevent any paracellular transport across the BBB.

The BBB is regarded as the major obstacle to overcome in the development of novel therapies for treating brain pathologies, and notably for the use of molecules that are likely to treat CNS disorders (Neuwelt et al., 2008, *Lancet Neurol.*, 7, 84-96).

One of the reasons that may explain why no effective treatment is currently available for the principal brain pathologies (brain cancer, Parkinson's and Alzheimer's diseases, stroke/cerebrovascular accidents (CVA), etc.) is that the developers of drug candidates for treating brain pathologies carry out in-house research programs (brain drug-discovery programs) while investing little effort in the problems of BBB crossing and in the preferential targeting of the CNS, and notably of the brain (brain drug-targeting programs) (Pardridge, 2003, *Mol. Interv.* 3. 90-105). Indeed, a drug candidate must follow certain structural, physicochemical, pharmacochemical and pharmacological rules in order to have the best chances of becoming a drug for treating a CNS pathology or disorder (Pajouhesh et al., 2005, *NeuroRx*, 2(4), 541-553). In the development of a drug candidate, the selectivity and specificity (pharmacological profiling) of a molecule for its target are essential to its therapeutic activity (efficacy). The bioavailability and potential toxicity (pharmaceutical profiling) of a molecule are crucial for its future as a drug. In other words, any molecule likely to become a drug for treating a CNS pathology or disorder must move across the BBB, maintain its biological activity, and exhibit suitable properties of pharmacokinetics (PK), absorption, distribution, metabolism and excretion/elimination (ADME) and pharmacodynamics (PD), with low toxicity (Tox). Thus, the hydrophilic/lipophilic balance of the molecule under development is particularly difficult to find for medicinal chemists in the CNS therapeutic area.

The major problem in treating CNS disorders and pathologies thus lies in the fact that the molecules administered do not cross the BBB and cannot thus reach to their target(s) in the CNS. The endothelial cells of the vessels and capillaries of the CNS, which are constitutive of the BBB, are an obstacle to molecules that cannot pass from the blood to the nervous tissue. Indeed, these endothelial cells and the astrocyte end-feet, which surround them, constitute a physical barrier related notably to the existence of tight junctions between endothelial cells which limit/prevent any passage/transport by the paracellular route, and also a physiological barrier, since these cells have effective efflux systems, which restrict any passage/transport by the transcellular route. These properties thus strongly limit the passage of substances from the blood plasma towards the brain extracellular space.

Indeed, some molecules capable of crossing the BBB are actively expelled/effluxed from the brain towards the bloodstream by multidrug resistant (MDR) transport proteins. These active efflux transport (AET) systems generally control the active efflux of small molecules from the brain towards the bloodstream. The model AET system at the BBB is the ATP binding cassette (ABC) transporter, namely P-glycoprotein (P-gp); however, other AET systems are present at the BBB, such as MDR-associated protein 1 (MRP1). P-gp, which is principally located on the luminal surface of brain capillary endothelial cells, is an essential element in the function of the physiological barrier of the BBB, preventing entry into the brain of most xenobiotics but also drug candidates and other molecules of therapeutic interest capable of being active in the CNS.

One of the priorities of research in the discovery of molecules for treating, diagnosing or imaging brain disorders or pathologies is thus to find means for increasing the effectiveness of passage of active substances across the BBB.

In this respect, strategies for the vectorisation of molecules across the BBB, currently studied and used by developers of drug candidates in order to enable a molecule of therapeutic interest to reach the CNS, can be divided into three principal strategies (FIG. 1) (Pardridge, 2007, *Pharm. Res.*, 24(9), 1733-1744; De Boer et al., 2007, *Clin. Pharmacokinet.*, 46(7), 553-576; De Boer et al., 2007, *Annu. Rev. Pharmacol. Toxicol.*, 47, 327-355; Jones et al., 2007, *Pharm. Res.*, 24(9). 1759-1771).

Neurosurgical Approaches

Neurosurgical approaches can be implemented by direct intraventricular injection in the brain, intracerebral injection or intrathecal infusion of the active substance, or by disruption of the BBB (temporary rupture of the integrity of the BBB). The main problem of neurosurgical approaches by intraventricular injection, apart from the costs relating to the neurosurgical procedure, is that the drug is not delivered directly in the brain parenchyma but in the cerebrospinal fluid. Indeed, intraventricular infusion involves placing a catheter in the ventricles (Aird, 1984, *Exp. Neurol.*, 86, 342-358). This highly invasive technique is not effective for the transport of active substances in the brain parenchyma. Indeed, the volume flow from the cerebrospinal fluid to the brain parenchyma during delivery of a drug by intraventricular infusion is governed by an abnormally slow diffusion of its convection (transport), because the brain does not have an intraparenchymal volumetric flow rate.

Similarly for intracerebral injection, the diffusion of an active substance in the brain decreases very quickly from the injection site to the site of the lesion. Indeed, the cerebral concentration of an active substance decreases by 90% at a distance of 500 μm from its injection site.

Intrathecal infusion involves placing a catheter in the brain connected to a pump which delivers the active substance with a predefined flow rate. Owing to the fact that the brain is the only organ that does not have a lymphatic system, normally serving to transport extracellular fluids back to general circulation, the distribution of an active substance by intrathecal infusion in the brain is very slow. This decreases the concentration of the active substance at the site of the lesion.

Moreover, risks of infection are significant during such neurosurgical procedures, notably by the presence of a catheter. Under these conditions, patient comfort is not optimal.

Temporary interruption of the impermeability of the BBB is associated with transitory opening of the tight junctions of brain capillary endothelial cells. This is the case for vasoactive substances such as leukotrienes or bradykinins (Baba et al., 1991, *J. Cereb. Blood Flow Metab.*, 11, 638-643). This strategy is equally invasive and requires arterial access to the carotid in sedated subjects/patients. The major problem encountered by the temporary rupture of the integrity of the BBB, besides expenses relating to the radiological procedure for access to the carotid, is that the BBB only remains open for a short period of time, thus limiting the possibility of delivering a drug over an extended period. Moreover, the temporary rupture of the BBB allows plasma proteins to enter the brain (whereas these proteins can be toxic for the brain) and can also facilitate the entry of infectious agents. This type of rupture of the BBB can thus lead to chronic neuropathologic disruptions and is associated with high risks of infection (Salahuddin et al., 1988, *Acta Neuropathol.*, 76, 1-10).

Pharmacological Approaches to Vectorisation

Pharmacological strategies for transporting molecules include transcellular diffusion of molecules made more lipophilic by adding lipid groups on the active substance (transcellular lipophilic diffusion or TLD) or the use of liposomes (Zhou et al., 1992, *J. Control. Release*, 19, 459-486), and transport by ionic adsorption via positively charged vector molecules or by cationisation of the active molecule (adsorptive-mediated transport or AMT).

Adding a lipid group enables the chemical conversion of hydrophilic molecules into more lipophilic molecules, notably through prodrug approaches. However, the synthesis of such compounds leads to molecules that exceed the optimal transport threshold to cross the BBB, notably with regard to molecular weight that becomes greater than the optimal limit of 450 Daltons (Pajouhesh et al., 2005, *NeuroRx*, 2(4), 541-553). For the same reason, liposomes or even small vesicles or nanoparticles (micelles, nanospheres, nanocapsules) are generally too large, not specific enough for the BBB, and consequently relatively ineffective for transporting molecules of therapeutic interest (or imaging or diagnostic agents, or any other molecule such as a molecular probe) across the BBB (Levin, 1980, *J. Med. Chem.*, 23, 682-684; Schackert et al., 1989, *Selective Cancer Ther.*, 5, 73-79). Thus, the main problems encountered by technologies of lipidisation (TLD) are their low specificity for specifically targeting and crossing the BBB compared to other cell membranes, the decrease in plasma values of the area under the curve (AUC) of the drug, and their generally limited use for vectorisation of small molecules.

In AMT approaches, the main problem encountered is the low specificity for targeting and crossing specifically the BBB compared to other cell membranes. Indeed, AMT is based on cationic molecules adsorbing on cells whose membranes are negatively charged, which is the case for most cells. The decrease in plasma values of the AUC of the drug, their generally limited use for vectorisation of small molecules, and their cytotoxicity are additional factors that penalize the AMT vectorisation approach.

Physiological Approaches to Vectorisation

Strategies based on physiological approaches to vectorisation consist of exploiting the various natural transport mechanisms of the BBB. These mechanisms of active transport of molecules across the BBB work either via coupling with a specific receptor substrate or by molecular mimicry with a specific receptor substrate (carrier-mediated transport or CMT), or via coupling or fusion with a ligand specifically targeting a receptor (receptor-mediated transport or RMT).

As an example, molecules such as L-DOPA (Parkinson's disease), melphalan (brain cancer), α-methyl-DOPA (arterial hypertension) and gabapentin (epilepsy) gain access to the brain by CMT via the large neutral amino-acid transporter (LAT1),(LAT1) (Pardridge, 2003, *Mol. Interv.*, 3, 90-105). These molecules have chemical structures close to phenylalanine, one of the natural substrates of LAT1. However, the main problems encountered by CMT approaches are their broad selectivity/specificity for conjugates that closely imitate/mimic the substrate of the endogenous receptor/transporter, and consequently their use remains limited to vectorisation of small molecules.

RMT calls upon a receptor-dependent transport system. Vectorisation is carried out via mechanisms of endocytosis by targeting the endogenous receptors/transporters present in brain capillaries. Notable examples of the various human BBB receptors involved in RMT include: transferrin receptor (TfR), insulin receptor (IR), low-density lipoprotein (LDL) receptors, which enable cholesterol transport, including LDL receptor (LDLR) and members of the family of low-density lipoprotein receptor-related protein (LRP), or insulin-like growth factor receptor (IGFR), diphtheria toxin receptor (DTR) or heparin binding epidermal growth factor-like growth factor (HB-EGF), as well as scavenger receptors (SCAV-Rs) including scavenger receptor class B type I (SR-BI). In RMT, the receptors on the membrane of a BBB endothelial cell bind their ligand, which leads to endocytosis of the complex composed of the receptor/transporter and its ligand in a vesicle, which forms on the cell surface and then penetrates the BBB endothelial cell. The ligand/receptor complex can pass through the endothelial cell (transcytosis), and thus can consequently cross the BBB to act in nervous tissue. This RMT process does not depend on the size of the molecule engulfed by endocytosis. Thus, RMT is a mechanism that enables transport from the blood to the brain of molecules such as insulin, iron transport proteins, cholesterol, various peptide derivatives and proteins, etc. For example, transferrin is used as a ligand vector of TfR present on the BBB (Jefferies et al., 1984, *Nature*, 312, 162-163; Friden et al., 1983, *Science*, 259, 373-377; Friden, 1994, *Neurosurgery*, 35, 294-298), and the molecule to be transported (active substance) is coupled with transferrin (ligand vector). Although this vectorisation strategy using a macromolecule enables an increase in the passage of the conjugate molecules of interest across the BBB, it has several disadvantages. First, the molecule is generally coupled to the vector by gene expression methods (fusion) thus limiting the number of molecules to be transported to only polypeptides or proteins. Second, the system for coupling the molecule with the vector is rather complex; traditional chemical or biochemical coupling does not yield well-defined macromolecular systems from a structural and molecular point of view.

SUMMARY OF THE INVENTION

The present invention overcomes these disadvantages. The invention shows that it is possible to design peptides or pseudo-peptides of reduced size capable of transporting across cell membranes, and more specifically across the BBB, substances of high molecular weight and/or large volume. The invention thus proposes novel peptides, conjugates and compositions that improve the bioavailability of molecules of interest, and notably improve their access (targeting) to the CNS.

More particularly, the inventors have developed peptide derivatives capable of binding human LDLR. The inventors have shown that these derivatives are capable of crossing the BBB. The inventors have also shown that these derivatives can transport, in BBB cells, molecules of therapeutic or diagnostic interest. Moreover, the inventors have developed peptides capable of binding LDLR without competition with the natural ligand, and thus without interference with LDL transport. These peptide derivatives thus represent novel products (vectors) that are particularly advantageous for the design and vectorisation of drugs or diagnostic agents, notably to reach the CNS.

The invention thus relates to a peptide or pseudo-peptide comprising a sequence of natural and/or non-natural amino acids, characterised in that it contains at most 30 amino acid residues and in that it binds human LDLR at the surface of cell membranes. The peptides comprise at least 5 amino acid residues, preferably at least 6, 7, or 8. In a preferred embodiment, the peptides of the invention also bind murine LDLR. In a particularly advantageous and preferred way, the peptides of the invention have the capacity to cross the BBB and potentially the membranes of cancerous or infectious cells.

The invention also relates to a conjugate comprising a peptide or pseudo-peptide such as defined above coupled to a substance of interest. As will be described below, the coupling is advantageously covalent and can be carried out so as to dissociate after crossing cell membranes, in order to release the substance of interest at a site of interest. According to the nature of the coupling, the substance can, for example, be released passively or under the action of enzymes or of given physiological conditions.

The invention also relates to a method/process for preparing a conjugate such as defined above.

The invention also relates to a pharmaceutical or diagnostic composition comprising a conjugate of the invention.

The invention also relates to the use of a peptide or pseudo-peptide, or a conjugate, such as defined above, for preparing a drug or a diagnostic or imaging agent.

The invention also relates to a method for improving or enabling the passage of a molecule across the BBB, comprising the coupling of this molecule to a peptide or pseudo-peptide such as defined above.

The invention also relates to an improved method for treating pathology in a subject by a drug, the improvement consisting of coupling this drug with a peptide or pseudo-peptide such as defined above.

The invention can be used in any mammal, notably any human being.

DESCRIPTION OF FIGURES

The patent or application file contains at least one drawing executed in color. Copies of this patent or patent application publication, with color drawings, will be provided by the Office upon request and payment of the necessary fee.

Diagram illustrating the various modes of passage of natural or pharmacological molecules across the BBB, adapted from Abbott and Romero, 1996, *Mol. Med. Today*, 2(3), 106-113.

FIGS. 2A-2B

Comparative diagram of synthesis in tandem (FIG. 2*a*) and synthesis via a linker (FIG. 2*b*) of a vector/molecule of therapeutic interest conjugate.

FIGS. 3A-3B

A—Diagram of the plasmid used for cloning hLDLR and mLDLR.

B—Diagram representing the fusion protein expressed by transfected cells.

FIG. 4

Western blot performed on CHO cell lines expressing constitutively hLDLR-GFP or GFP (control) fusion proteins. A 190 kDa band corresponding to the size of the hLDLR-GFP fusion protein is detected with anti-hLDLR antibody.

Figure 1:
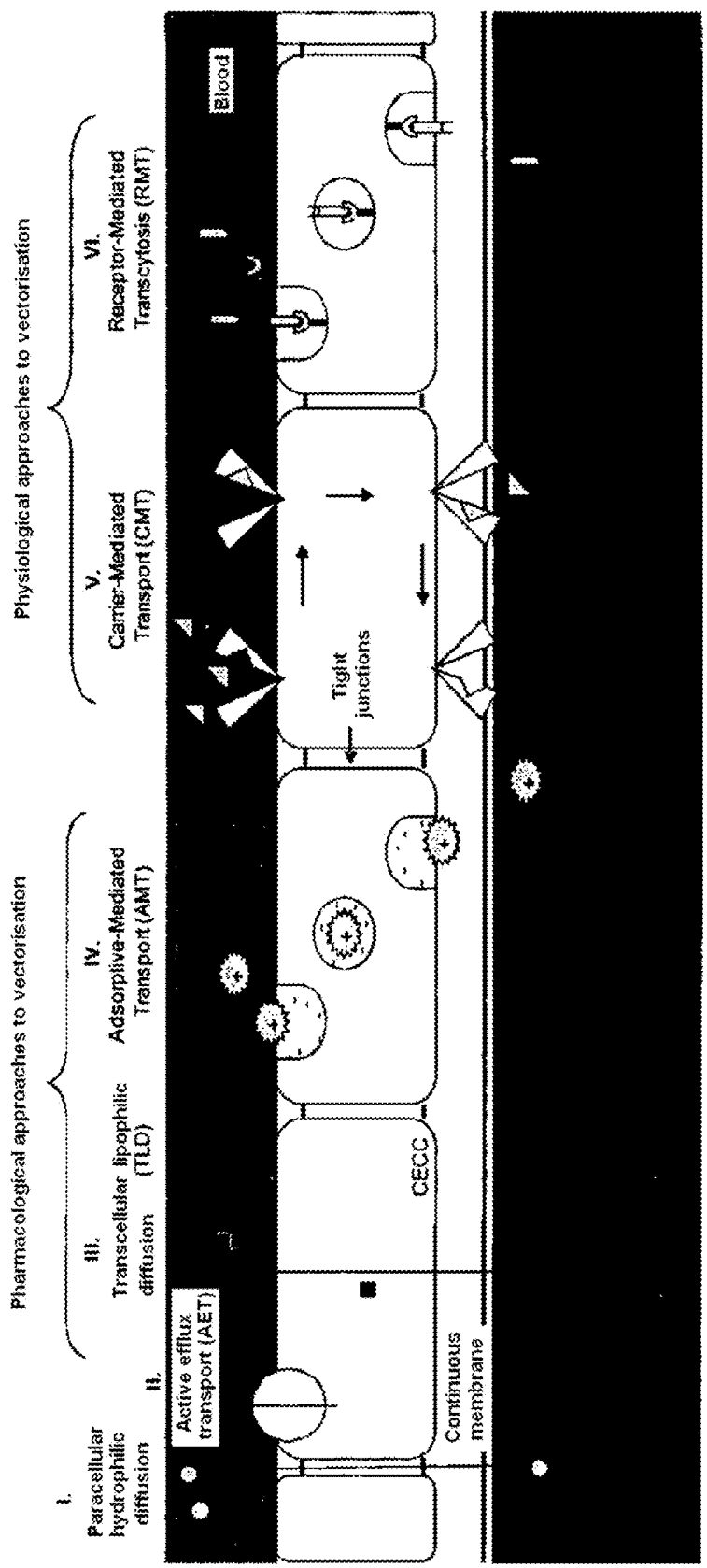
FIG. 1

FIGS. 5A1-A4 and 5B1-B4

Immunocytochemistry on non-permeabilised CHO cells, stably expressing either A—GFP alone (control), or B—the hLDLR-GFP construction. Cell nuclei are stained with Hoechst (blue, A1 and B1). GFP fluorescence is visible in green (A2 and B2), that of the staining of the extracellular domain of hLDLR by anti-hLDLR antibody is visible in red (A3 and B3) and the superimposing of red and green stains is visible in yellow/orange (A4 and B4). Note that only the cells stably transfected with the hLDLR-GFP construction express the membrane receptor (B3).

FIGS. 6A-6C

A—Cells of the CHO-hLDLR-GFP cell line expressing hLDLR-GFP (green) incubated with DiI-LDL (red) red): the superimposing of red and green stains is visible in yellow/orange: note the strong staining of the cells.

B—Cells of a CHO-TfR-GFP cell line expressing hTfR-GFP (green) incubated with DiI-LDL (red): absence of DiI-LDL binding and endocytosis.

C—Cells of the CHO-hLDLR-GFP cell line expressing hLDLR-GFP (green) incubated with transferrin coupled to Texas Red (red): absence of Tf ligand binding and endocytosis.

Note the difference in intensity of staining between A on the one hand, and B and C on the other hand, where only the staining of hTfr and hLDLR receptors fused with GFP is detected.

FIGS. 7A1-A4 and 7B1-B4

CHO cell lines stably expressing A—GFP alone (green), and B—hLDLR-GFP (green), and immunostaining with an anti-viral envelope protein antibody of a clone of bacterial viruses expressing a peptide (SEQ ID NO: 1) with affinity for hLDLR (red dots). Cell nuclei are stained with Hoechst (blue, A1 and B1). GFP fluorescence is visible in green (A2 and B2), that of the staining of the viral envelope of the bacterial virus by the viral anti-protein antibody is visible in red (A3 and B3) and the superimposing of red and green stains is visible in yellow/orange (A4 and B4). Note that the cells that do not express hLDLR in A do not bind bacterial viruses.

FIGS. 8A-8D

Comparison by immunocytochemistry of the binding of control bacterial viruses (A-C) and of bacterial viruses expressing peptides with affinity for hLDLR (SEQ ID NO: 1) (B, D), on human fibroblasts (A-B) and on porcine brain microvascular endothelial cells (C-D). The bacterial viruses are visualised with an anti-viral envelope protein antibody.

FIGS. 9A-9C

Evaluation by FACS of the interaction between CHO-hLDLR-GFP cells and a clone of bacterial viruses expressing peptide SEQ ID NO: 11 with affinity for hLDLR compared with control bacterial viruses not expressing peptides with affinity for this receptor. The signal in Q2 shows on the cells a combination of two signals, which are positive on the one hand if hLDLR-GFP is expressed (GFP fluorescence, horizontal axis) and on the other hand if bacterial viruses with affinity for this receptor are bound to cells via the peptides that they express (immunocytochemical staining, vertical axis).

A—CHO-hLDLR-GFP cells incubated with anti-viral envelope protein antibody and its secondary antibody APC.

B—CHO-hLDLR-GFP cells incubated with negative control bacterial viruses, anti-viral envelope protein antibody and its secondary antibody APC.

C—CHO-hLDLR-GFP cells incubated with a clone of bacterial viruses expressing a peptide with affinity for hLDLR (SEQ ID NO: 11), anti-viral envelope protein antibody and its secondary antibody APC. A significant shift of the signal is observed in Q2.

FIGS. 10A-10D

Evaluation by FACS of the interaction between human fibroblasts and a clone of bacterial viruses expressing peptide SEQ ID NO: 12 with affinity for hLDLR, compared with control bacterial viruses not expressing peptides with affinity for this receptor. The signal in Q2 shows on the cells a combination of two signals, which are positive on the one hand if hLDLR is expressed (immunocytochemical staining, horizontal axis) and on the other hand if bacterial viruses with affinity for this receptor are bound to cells via the peptides that they express (immunocytochemical staining, vertical axis).

A—Human fibroblasts incubated with anti-viral envelope protein antibody and its secondary antibody APC.

B—Human fibroblasts incubated with anti-LDLR antibody and its secondary antibody Alexa 488.

C—Human fibroblasts incubated with negative control bacterial viruses, anti-viral envelope protein antibody, anti-LDLR antibody and secondary antibodies APC and Alexa 488.

D—Human fibroblasts incubated with a clone of bacterial viruses expressing peptide SEQ ID NO: 12 with affinity for hLDLR, anti-viral envelope protein antibody, anti-LDLR antibody and secondary antibodies APC and Alexa 488. A significant shift of the signal is observed in Q2.

FIGS. 11A-11E

Evaluation by FACS of the interaction between HUVEC and two clones of bacterial viruses expressing peptides, one cyclic (SEQ ID NO: 11), the other linear (SEQ ID NO: 21), with affinity for hLDLR, compared with control bacterial viruses not expressing peptides with affinity for this receptor.

A—HUVEC incubated with anti-viral envelope protein antibody and its secondary antibody APC.

B—HUVEC incubated with anti-LDLR antibody and its secondary antibody Alexa 488.

C—HUVEC incubated with negative control bacterial viruses, anti-viral envelope protein antibody, anti-LDLR antibody and secondary antibodies APC and Alexa 488.

D—HUVEC incubated with a clone of bacterial viruses expressing cyclic peptide (SEQ ID NO: 11) with affinity for hLDLR, anti-viral envelope protein antibody, anti-LDLR antibody and secondary antibodies APC and Alexa 488. A significant shift of the signal is observed in Q2.

E—HUVEC incubated with a clone of bacterial viruses expressing linear peptide (SEQ ID NO: 21) with affinity for hLDLR, anti-viral envelope protein antibody, anti-LDLR antibody and secondary antibodies APC and Alexa 488. A significant shift of the signal is observed in Q2.

FIGS. 12A-12I

Evaluation by FACS on HUVEC of competition between the peptides expressed by the bacterial viruses with affinity for LDLR and its natural ligand LDL.

A—HUVEC incubated with anti-viral envelope protein antibody and its secondary antibody APC.

B—HUVEC incubated with anti-LDLR antibody and its secondary antibody Alexa 488.

C—HUVEC incubated with negative control bacterial viruses, anti-viral envelope protein antibody, anti-LDLR antibody and secondary antibodies APC and Alexa 488.

D—HUVEC incubated with negative control bacterial viruses, anti-viral envelope protein antibody, anti-LDLR antibody, LDL, and secondary antibodies APC and Alexa 488. No effect is observed due to the presence of LDL.

E—HUVEC incubated with a clone of bacterial viruses expressing linear peptide (SEQ ID NO: 21) with affinity for hLDLR, anti-viral envelope protein antibody, anti-LDLR antibody and secondary antibodies APC and Alexa 488.

F—HUVEC incubated with a clone of bacterial viruses expressing linear peptide (SEQ ID NO: 21) with affinity for hLDLR, anti-viral envelope protein antibody, anti-LDLR antibody, LDL, and secondary antibodies APC and Alexa 488. LDL strongly decreases the binding of SEQ ID NO: 21 peptides expressed by the bacterial viruses.

G—HUVEC incubated with a clone of bacterial viruses expressing cyclic peptide (SEQ ID NO: 11) with affinity for hLDLR, anti-viral envelope protein antibody, anti-LDLR antibody and secondary antibodies APC and Alexa 488.

H—HUVEC incubated with a clone of bacterial viruses expressing cyclic peptide (SEQ ID NO: 11) with affinity for hLDLR, anti-viral envelope protein antibody, anti-LDLR antibody, LDL, and secondary antibodies APC and Alexa 488. No effect is observed due to the presence of LDL.

I—Graph representing the percentage of shift of the fluorescence signal in zone Q2 of graphs A-H obtained by FACS. No shift is measured in Q2 for the control bacterial viruses that do not express peptides with affinity for hLDLR. For the bacterial viruses expressing peptide SEQ ID NO: 21, more than 55.8% of the signal shifts in Q2 indicating affinity of the peptides expressed by these bacterial viruses for HUVEC hLDLR. Adding LDL leads to an 85% loss of signal in Q2 in the control bacterial viruses, indicating competition between the bacterial virus corresponding to peptide sequence SEQ ID NO: 21 and LDL at the site where LDL binds to hLDLR. The equally strong signal in Q2 of the bacterial viruses that express peptide SEQ ID NO: 11 (shift greater than 70% compared to control bacterial viruses) is only slightly shifted (17%) by adding LDL.

FIGS. 13A-13D

Double immunofluorescent staining of frozen sections of C57BL6 mouse brain, 2 h after mouse tail vein injection of control bacterial viruses (A-B) and bacterial viruses expressing a peptide (SEQ ID NO: 1) with affinity for hLDLR and mLDLR (C-D). Brain vessels are stained with anti-mouse IgG, in green (A-C); bacterial viruses are stained with anti-viral envelope protein antibody, in red (B-D).

FIG. 14

General scheme of synthesised peptides conjugated with rhodamine or S-Tag, with a C-terminus (C-term) spacer/linker.

FIGS. 15A1-A3, 15B1-B3 and 15C1-C3

Evaluation by fluorescence and immunocytochemistry of binding and endocytosis of peptides with affinity for hLDLR (SEQ ID NO: 1/rhodamine in A and SEQ ID NO: 2/S-Tag in C) on cells of the CHO-hLDLR-GFP cell line compared with a control peptide (in B). GFP fluorescence is visible in green (A1, B1 and C1); that related to peptides, visualised by rhodamine or by binding of an anti-S-Tag antibody coupled to Alexa594 is visible in red (A2, B2 and C2); and the superimposing of red and green stains is visible in yellow/orange (A3, B3 and C3). Note the high levels of intracellular staining in red with peptides SEQ ID NO: 1/rhodamine in A2 and SEQ TD NO: 2/S-Tag in C2, and the superimposing of hLDLR-GFP staining (green, A1, C1) with peptides bound or internalised by endocytosis (A2, C2).

FIGS. 16A-16D

Quantification of binding rates (A-C) and endocytosis (B-D) of peptides SEQ ID NO: 11 and SEQ ID NO: 2 and of control peptide on CHO-hLDLR-RFP cell line (A-B) and human fibroblasts (C-D), respectively.

FIGS. 17A-17C

Immunocytochemical evaluation of the interaction between CHO-hLDLR-GFP cells and peptide SEQ ID NO: 11 with affinity for hLDLR, conjugated with S-Tag, compared with a control peptide also conjugated with S-Tag. The signal in Q2 shows on the cells a combination of two signals, which are positive on the one hand if hLDLR-GFP is expressed (GFP fluorescence, horizontal axis) and on the other hand if the control peptide and peptide SEQ ID NO: 11 with affinity for this receptor are bound to the cells (immunocytochemical staining, vertical axis).

A—Cells incubated with secondary antibody APC.

B—Cells incubated with control peptide conjugated with S-Tag, anti-S-Tag antibody and secondary antibody APC.

C—Cells incubated with peptide SEQ ID NO: 11 with affinity for LDLR conjugated with S-Tag, anti-S-Tag antibody and secondary antibody APC. A significant shift of the signal is observed in Q2.

FIG. 18

Evaluation of the toxicity of peptides on a barrier of endothelial cells in the in vitro BBB model by co-incubation with Lucifer Yellow (LY, fluorimetric analysis) and analysis of the rate of passage of LY as a function of time and in the absence or presence of a control peptide and peptide SEQ ID NO: 1, both conjugated with rhodamine.

FIG. 19

Evaluation of cells after lysis and fluorimetric analysis of rates of binding to endothelial cells of the in vitro BBB model and/or internalisation in these cells of a control peptide and peptide SEQ ID NO: 1, both conjugated with rhodamine.

FIG. 20

Fluorimetric evaluation of rates of passage (permeability, Pe) across the endothelial cells of an in vitro BBB model of a control peptide and peptide SEQ ID NO: 1, both conjugated with rhodamine. LY Pe measurements are used to verify the integrity of in vitro BBB models.

DETAILED DESCRIPTION OF THE INVENTION

The invention relates to peptide derivatives capable of binding human LDLR and use thereof in the field of pharmaceuticals, notably to transport, in BBB cells, molecules of therapeutic or diagnostic interest.

Human LDLR is a transmembrane protein of 839 amino acids comprising three regions: the extracellular region (1-768), the transmembrane region (768-790) and the cytoplasmic region (790-839). The extracellular region is divided into two subregions: that of LDL binding (1-322) and that outside the LDL binding region (322-768) (see WO2007/014992).

The brain has a great need for LDL to function properly. The natural ligands of LDLR are LDL and more particularly the apolipoprotein B (ApoB) and apolipoprotein E (ApoE) components of LDL particles, which thus enable the transport of cholesterol contained in these particles across cell membranes and more particularly across the BBB.

It has thus been shown that LDLR enabled the transcytosis of LDL particles across the BBB (Dehouck et al., 1997, *J. Cell Biol.*, 138(4), 877-889), via an RMT process, in specific endosomal vesicles that prevent fusion with the lysosome. These lipoproteins, having crossed the BBB by transcytosis, are then taken up by neurons and/or astrocytes (Spencer et al., 2007, *Proc. Natl. Acad. Sci. USA*, 104(18), 7594-7599). This property was used to vectorise molecules of therapeutic interest by nanoparticles on which are conjugated whole apolipoproteins (LDL components) (Kreuter et al., 2007, *J. Control. Release*, 118, 54-58). In this study, however, a whole apolipoprotein was used, in a form coupled to a nanoparticle in order to mimic LDL particle structure.

Figure 2:
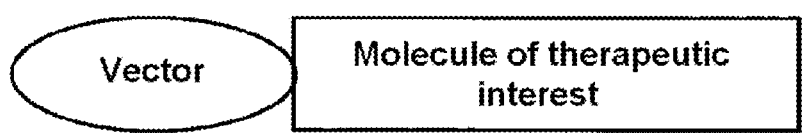
Figure 2:
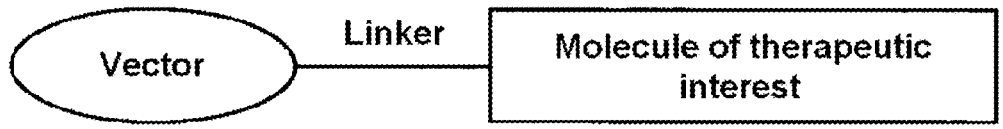

The present invention shows, for the first time, that it is possible to design small peptides capable of binding LDLR and of crossing the BBB. The invention provides many advantages compared to strategies of the prior art, which follow notably from the choice of receptor and the design strategy and nature of the peptides. The invention shows that such peptides or pseudo-peptides are selective for some cell membranes and can be used to deliver small chemical molecules (whether lipophilic or not) as well as macromolecules such as proteins of therapeutic interest. Peptide or pseudo-peptide vectors can be easily synthesised chemically, and most molecules of therapeutic interest or imaging or diagnostic agents can be coupled with the peptide or pseudo-peptide vector simply and effectively through a prodrug strategy via a spacer (synthesis via a linker) or by direct coupling (synthesis in tandem) between the two entities (FIG. 2). The peptides and pseudo-peptides of the invention can be designed to adopt a cyclic configuration, thus more resistant to proteolysis. Moreover, the peptides and pseudo-peptides of the invention can be designed to bind LDLR without competition with the natural ligand. The invention indeed led to the discovery of a novel binding site on LDLR, different from the LDL binding site. As a result, use of the peptides and pseudo-peptides of the invention targeting this site enables effective transport without substantial disruption of the binding of the natural ligand.

The research carried out within the scope of the present invention has enabled the Applicant to show that the linear or cyclic peptides or pseudo-peptides that the Applicant developed can be used as vectors for molecules of therapeutic interest, or for imaging or diagnostic agents, or for any other molecule such as a molecular probe, in the treatment, imaging and/or diagnosis of neurological pathologies, as well as infectious or cancerous pathologies of the brain or other tissues/organs.

The linear or cyclic peptides or pseudo-peptides described in the present invention have the capacity to target cell receptors/transporters and particular cell types and/or to cross cell membranes, notably those of the physiological barriers of the brain and more particularly the BBB or the blood-retinal barrier (BRB).

The linear or cyclic peptides or pseudo-peptides described in the present invention have the capacity to target cell receptors/transporters and particular cell types, notably cancer cells, nervous or non-nervous tissue and/or to cross cell membranes, notably those of the physiological barriers of the CNS and more particularly the blood-tumour barrier (BTB) of nervous tissue tumours.

The linear or cyclic peptides or pseudo-peptides described in the present invention have the capacity to target cell receptors/transporters and particular cell types and/or to cross cell membranes, notably those of the physiological barriers of the CNS, to treat more particularly infectious brain pathologies or other pathologies of a bacterial, viral, parasitic or fungal nature.

The linear or cyclic peptides or pseudo-peptides described in the present invention have the capacity to bind to a murine or human LDLR of the cell membrane and to cross the aforesaid membrane via this receptor by transcytosis.

The linear or cyclic peptides or pseudo-peptides described in the present invention have the capacity to bind to LDLR at the surface of cell membranes of physiological barriers of the murine and human brain and to cross the aforesaid physiological barrier via LDLR by RMT.

The invention thus more particularly relates to peptides and pseudo-peptides that have an affinity for LDLR, and use thereof as vectors for molecules of therapeutic interest or for imaging or diagnostic agents, or for any other molecule such as a molecular probe. Such peptides can be used in many indications, notably in the treatment, imaging and/or diagnosis of neurological pathologies and of infectious or cancerous pathologies of the brain or other tissues/organs.

The invention thus relates to a peptide or pseudo-peptide comprising a sequence of natural and/or non-natural amino acids, characterised in that it contains at most 30 amino acid residues, preferably at most 25, and in that it binds human LDLR at the surface of cell membranes. In the context of the invention, the term "peptide" or "pseudo-peptide" designates a molecule comprising a chain/sequence of amino acid residues, which can be natural or non-natural, optionally modified or functionalised, and bound together by peptide, non-peptide or modified peptide bonds. The peptides can be cyclic or non-cyclic and can have, if need be, one or more protected ends (N- and/or C-terminus).

The invention more preferably relates to a peptide or pseudo-peptide such as defined above, characterised in that it has the capacity to cross the BBB.

In a first embodiment, the peptides or pseudo-peptides of the invention are of general formula (I) as follows:

X-M-P-R-Y        (I)

wherein:
X is a group comprising 1 to 11 consecutive natural and/or non-natural amino acids,
Y is a group comprising 1 to 11 consecutive natural and/or non-natural amino acids,
X and/or Y contain(s) at least one amino acid residue enabling the formation of a cycle within the peptide,
M designates methionine or an isostere thereof or an analogue thereof,
P designates proline or an isostere thereof or an analogue thereof,
R designates arginine or an isostere thereof or an analogue thereof, and wherein the total number of amino acid residues is less than or equal to 25.

Advantageously, in the peptides or pseudo-peptides of formula (I), X is a group of formula $(Xaa)_iZ(Xaa)_j$ and Y is a group of formula $(Xaa)_kW(Xaa)_l$, wherein Xaa represents a natural or non-natural amino acid, including an amino acid of D-configuration, a non-coded amino acid, or an amino acid containing a peptidomimetic bond, Z and W represent two identical or different amino acids enabling the cyclisation of the peptide, and i, j, k and l are integers, identical or different, between 0 and 5.

The invention results notably from the identification, by comparison strategies of peptide ligand sequences, of motifs that ensure LDLR binding and transport but without competition with the natural ligand. The absence of competition with the natural ligand shows that the binding motifs discovered by the Inventors involve a novel binding site on LDLR, which constitutes an unexpected and particularly advantageous discovery in the context of vectorisation of compounds in vivo.

The natural or non-natural amino acids constitutive of the X and Y groups of the peptides or pseudo-peptides of the invention can be identical or different and can be selected from:
glycine (Gly, G) or 2-aminoethanoic acid, sarcosine (Sar) or N-methylglycine (MeGly), N-ethylglycine (EtGly), allylglycine (allylGly) or 2-aminopent-4-enoic acid, 2-cyclopentylglycine (Cpg), 2-cyclohexylglycine (Chg), 2,2-dipropylglycine (Dpg), 2-(3-indolyl)glycine (IndGly), 2-indanylglycine (Igl), 2-neopentylglycine (NptGly), 2-octylglycine (OctGly), 2-propargylglycine (Pra) or 2-aminopent-4-ynoic acid, 2-phenylglycine (Phg), 2-(4-chlorophenyl)glycine, azaglycine (AzGly), glycinol or 2-aminoethanol,
alanine (Ala, A) or 2-aminopropanoic acid, beta-alanine (β-Ala) or 3-aminopropanoic acid, dehydroalanine, N-methylalanine, 3-cyclopropylalanine (Cpa), 3-cyclohexylalanine (Cha), 3-cyclopentylalanine, 3-(1-naphthyl)alanine (1Nal), 3-(2-naphthyl)alanine (2Nal), 3-(3-pyridyl)alanine, 3-(2-thienyl)alanine (Thi), alaninol or 2-aminopropanol, valine (Val, V) or 2-amino-3-methylbutanoic acid, N-methylvaline (MeVal), norvaline (Nva) and methylated and/or hydroxylated derivatives thereof, 5-hydroxynorvaline (Hnv) and derivatives thereof, 3-mercaptovaline (penicillamine, Pen), valinol or 2-amino-3-methylbutanol, leucine (Leu, L) or 2-amino-4-methylpentanoic acid, norleucine (Nle) or 2-aminohexanoic acid, 3-hydroxyleucine, 6-hydroxynorleucine, tert-leucine (Tle) or 2-amino-3,3-dimethylbutanoic acid, homoleucine or 3-amino-5-methylhexanoic acid, 2,3-dehydroleucine, leucinol or 2-amino-4-methylpentanol, isoleucine (Ile, I) or 2-amino-3-methylpentanoic acid, allo-isoleucine (alle or Allo-Ile), N-methylisoleucine (MeIle), isoleucinol or 2-amino-3-methylpentanol, aspartic acid (Asp, D) or 2-aminobutanedioic acid and esterified or amidated side-chain derivatives thereof, 3-methylaspartic acid, aspartinol, asparagine (Asn, N) or 2-amino-3-carbamoylpropanoic acid or 2-aminosuccinamic acid and N-substituted derivatives thereof, N-ethylasparagine (EtAsn), asparaginol, glutamic acid (Glu, E) or 2-aminopentanedioic acid and esterified or amidated side-chain derivatives thereof, pyroglutamic acid (Pyr) or pidolic acid or 5-oxoproline, gamma-carboxyglutamic acid or 4-carboxyglutamic acid (Gla), glutarinol, glutamine (Gln, Q) or 2-amino-4-carbamoylbutanoic acid and N-substituted derivatives thereof, glutaminol, diaminoethanoic acid, 2,3-diaminopropanoic acid (Dpr or Dap), 3-mercaptopropanoic acid (Mpa), 2-amino-3-guanidinopropanoic acid (Agp), 2-aminobutanoic acid (Abu), 4-aminobutanoic acid (4Abu) or GABA, 2-aminoisobutanoic acid (Aib), 3-aminoisobutanoic acid (bAib), 2,4-diaminobutanoic acid (Dab), 3,4-diaminobutanoic acid (Dbu), 2-amino-4-cyanobutanoic acid (Cba), 2-amino-4-guanidinobutanoic acid (Agb), 5-aminopentanoic acid (Ava), 4-amino-3-hydroxy-5-phenylpentanoic acid (AHPPA), 4-amino-5-cyclohexyl-3-hydroxypentanoic acid (ACHPA), 6-aminohexanoic acid (Acp or Ahx), para-aminobenzoic acid (PABA), meta-aminomethylbenzoic acid or 3-aminomethylbenzoic acid, para-aminomethylbenzoic acid (PAMBA) or 4-aminomethylbenzoic acid, 2-aminoadipic acid (Aad) or 2-aminohexanedioic acid, 3-aminoadipic acid (bAad) or 3-aminohexanedioic acid, 2-aminopimelic acid (Apm) or 2-amino-heptanedioic acid (Ahe), 4-amino-3-hydroxy-6-methylheptanoic acid or statine (Sta), 2,2-diaminopimelic acid (Dpm) or 2,2-diamino-heptanedioic acid, desmosine (Des) or 2-amino-6-[4-(4-amino-4-carboxybutyl)-3,5-bis-(3-amino-3-carboxypropyl)-pyridin-1-yl]hexanoic acid, isodesmosine (Ide) or 2-amino-6-[2-(4-amino-4-carboxybutyl)-3,5-bis-(3-amino-3-carboxypropyl)-pyridin-1-yl]hexanoic acid, ornithine (Orn) or 2,5-diaminopentanoic acid and epsilon-aminated or amidated derivatives thereof, canaline or 2-amino-4-(aminooxy)butanoic acid, ornithinol, lysine (Lys, K) or 2,6-diaminohexanoic acid and epsilon-aminated or amidated derivatives thereof, homolysine or 2,7-diaminoheptanoic acid (hLys), 5-hydroxylysine (Hyl) or 2,6-diamino-5-hydroxyhexanoic acid, allo-hydroxylysine (aHyl), 6-N-methyllysine (MeLys), S-aminoethylcysteine or 2-amino-3-(2-aminoethylthio)propanoic acid, 3-methyl-S-aminoethylcysteine or 2-amino-3-(2-aminoethylthio)butanoic acid, lysinol, arginine (Arg, R) or 2-amino-5-guanidinopentanoic acid or 2-amino-5-(diaminomethylidene amino)pentanoic acid, homoarginine or 2-amino-6-guanidinohexanoic acid, N-hydroxyarginine, citrulline (Cit) or 2-amino-5-(carbamoylamino)pentanoic acid, 2-amino-5-(4-carbamimidoylphenyl)pentanoic acid, 2-amino-5-(1H-imidazol-2-ylamino)pentanoic acid, canavanine or 2-amino-4-(guanidinooxy)butanoic acid, argininol, histidine (His, H) or 2-amino-3-(1H-imidazol-4-yl)propanoic acid and N-substituted derivatives thereof, histidinol, serine (Ser, S) or 2-amino-3-hydroxypropanoic acid and O-substituted derivatives thereof (ethers, etc.), 2-amino-4-hydroxybutanoic acid or homoserine (Hse) and O-substituted derivatives thereof (ethers, etc.), serinol or 2-amino-propan-1,3-diol, threonine (Thr, T) or 2-amino-3-hydroxybutanoic acid and O-substituted derivatives thereof (ethers, etc.), allo-threonine (allo-Thr) and O-substituted derivatives thereof (ethers, etc.), threoninol (Thol), phenylalanine (Phe, F) or 2-amino-3-phenylpropanoic acid, 2-fluorophenylalanine, 3-fluorophenylalanine, 4-fluorophenylalanine, 3,4-difluorophenylalanine, pentafluorophenylalanine, 2-chlorophenylalanine, 3-chlorophenylalanine, 4-chlorophenylalanine, 3,4-dichlorophenylalanine, 4-bromophenylalanine, 3-iodophenylalanine, 4-iodophenylalanine, 4-nitrophenylalanine, 2-methoxyphenylalanine, 3-methoxyphenylalanine, 4-methylphenylalanine, 4-aminophenylalanine, 4-guanidinophenylalanine, 3,4-dihydroxyphenylalanine or DOPA, 2-amino-4-phenylbutanoic acid or homophenylalanine, 4-biphenylylalanine (Bip), 4-benzoylphenylalanine (Bpa), phenylalaninol (Phol), tyrosine (Tyr, Y) or 2-amino-3-(p-hydroxyphenyl)propanoic acid and O-substituted derivatives thereof (ethers, etc.), 3-iodotyrosine, 3,5-diiodotyrosine, 2-bromotyrosine, 3,5-dibromotyrosine, 2,6-dimethyltyrosine, 3-nitrotyrosine, 3-sulphotyrosine, tyrosinol or 2-amino-4-hydroxybenzenepropanol, tryptophan (Trp, W) or 2-amino-3-(1H-indol-3-yl)propanoic acid and N-substituted derivatives thereof, 2-methyltryptophane, 5-hydroxytryptophane (5-HTP), tryptophanol, cysteine (Cys, C) or 2-amino-3-mercaptopropanoic acid and S-substituted derivatives thereof, S-acetylcysteine or 2-amino-3-(acetylthio)propanoic acid, selenocysteine (Sec, U) or 2-amino-3-(seleno)propanoic acid, cysteinol, methionine (Met or M) or 2-amino-4-(methylthio)butanoic acid, homomethionine or 3-amino-5-(methylthio)pentanoic acid, methioninol, proline (Pro, P) or pyrolidine-2-carboxylic acid, homoproline or 2-(2-pyrrolidinyl)ethanoic acid, 3-hydroxyproline (3Hyp), 4-hydroxyproline (4Hyp), 3-methylproline, 3,4-dehydroproline, 3,4-methanoproline, 4-aminoproline, 4-oxoproline, thioproline or thiazolidine-4-carboxylic acid (Thz), 2-oxothiazolidine-4-carboxylic acid, indolin-2-carboxylic acid (Idc), pipecolic acid (Pip) or piperidine-2-carboxylic acid, nipecotic acid (Nip) or piperidine-3-carboxylic acid, 4-oxopipecolic acid, 4-hydroxypipecolic acid, amino-1-cyclohexanecarboxylic acid, prolinol.

As indicated, peptides comprising at least one amino acid residue, preferably two amino acid residues capable of enabling cyclisation of the peptide are preferred. Such amino acids are typically selected from Cys, Mpa, Pen, dehydroalanine, or allylGly.

Cyclisation is typically obtained by the formation of a disulphide bridge between two cysteine (or Pen) residues, one in group X, the other in group Y. A cysteine in the N-terminus (N-term) position can in addition be replaced by Mpa for cyclisation via a disulphide bridge.

A cysteine residue can also be replaced by dehydroalanine, for cyclisation via a lanthionine bridge, or by allylGly for cyclisation by metathesis via a dicarba bridge.

A lactam bridge can be created between the side acid function of a Glu (or Asp) residue and a side amine function of a Lys or an N-term amine. Similarly, cyclisation between the N-term amine function and the C-terminus or C-term acid function (head/tail) can be carried out via an amide bond, just as cyclisation between the side amine function of a Lys and the C-term acid function of the peptide.

Preferably, in the peptides or pseudo-peptides of formula (I), at least one of groups X and Y contain a cysteine residue.

In a particularly preferred embodiment, residues Z and W each represent cysteine.

As indicated, M represents a methionine residue, or an isostere thereof or an analogue thereof. The methionine isosteres or analogues are preferably selected from Nle, homomethionine, Pen and Mpa.

As indicated, P represents a proline residue, or an isostere thereof or an analogue thereof. The proline isosteres or analogues are preferably selected from cyclopentene isosteres, 3,4-dehydroproline, 3,4-methanoproline, homoproline, 3Hyp, 4Hyp, 3-methylproline, 4-aminoproline, 4-oxoproline, Thz, 2-oxothiazolidine-4-carboxylic acid, Idc, Pip, Nip, 4-oxopipecolic acid, 4-hydroxypipecolic acid and amino-1-cyclohexanecarboxylic acid.

As indicated, R represents an arginine residue, or an isostere thereof or an analogue thereof. The arginine isosteres or analogues are preferably selected from homoarginine, N-hydroxyarginine, Agp, Agb, Cit, 2-amino-5-(4-carbamimidoylphenyl) pentanoic acid, 2-amino-5-(1H-imidazol-2-ylamino)pentanoic acid, Orn, Lys and isosteres/analogues thereof, S-aminoethylcysteine, 3-methyl-S-aminoethylcysteine, hLys, Hyl, aHyl, MeLys, His and isosteres/analogues thereof, Nle, diaminoethanoic acid, Dpr and Dbu.

Particularly preferred among the peptides or pseudo-peptides of formula (I) are those wherein:
i is an integer selected from 0, 1, 3 or 4; and/or
j is an integer selected from 0, 3 or 4; and/or
k is an integer selected from 0, 1 or 3; and/or
l is an integer selected from 0, 1 or 3.

The preferred peptides or pseudo-peptides in the context of the invention are of the general formula (Xaa)$_i$-Cys-(Xaa)$_j$-Met-Pro-Arg-(Xaa)$_k$-Cys-(Xaa)$_l$, wherein Xaa designates any natural or non-natural amino acid residue and i, j, k and l are integers, identical or different, between 0 and 5. Preferably, i=0, 1, 3 or 4; j=0, 3 or 4; k=0, 1 or 3; and/or l=0, 1 or 3.

Particular examples of the peptides of the invention of formula (I) are described in sequences SEQ ID NO: 1 to SEQ ID NO: 11 and SEQ ID NO: 30 to SEQ ID NO: 65 as follows:

HLDCMPRGCFRN;, SEQ ID NO: 1

ACQVKSMPRC;, SEQ ID NO: 2

ACTTPMPRLC;, SEQ ID NO: 3

ACKAPQMPRC;, SEQ ID NO: 4

ACLNPSMPRC;, SEQ ID NO: 5

ACLVSSMPRC;, SEQ ID NO: 6

ACLQPMPRLC;, SEQ ID NO: 7

ACPVSSMPRC;, SEQ ID NO: 8

ACQSPMPRLC;, SEQ ID NO: 9

ACLTPMPRLC;, SEQ ID NO: 10

DSGLCMPRLRGCDPR;, SEQ ID NO: 11

ACMPRLRGCA;, SEQ ID NO: 30

ASGLCMPRLRGCDPR;, SEQ ID NO: 31

DAGLCMPRLRGCDPR;, SEQ ID NO: 32

DSALCMPRLRGCDPR;, SEQ ID NO: 33

DSGACMPRLRGCDPR;, SEQ ID NO: 34

DSGLCMPRARGCDPR;, SEQ ID NO: 35

DSGLCMPRLAGCDPR;, SEQ ID NO: 36

DSGLCMPRLRACDPR;, SEQ ID NO: 37

DSGLCMPRLRGCAPR;, SEQ ID NO: 38

DSGLCMPRLRGCDAR;, SEQ ID NO: 39

DSGLCMPRLRGCDPA;, SEQ ID NO: 40

SGLCMPRLRGCDPR;, SEQ ID NO: 41

GLCMPRLRGCDPR;, SEQ ID NO: 42

CMPRLRGC;, SEQ ID NO: 43

CMPRARGC;, SEQ ID NO: 44

CMPRLAGC;, SEQ ID NO: 45

CMPRLRAC;, SEQ ID NO: 46

CMPRLKGC;, SEQ ID NO: 47

-continued (D)-CMPRLRGC;, SEQ ID NO: 48

CMPR-(D)-LRGC;, SEQ ID NO: 49

CMPRL-(D)-RGC;, SEQ ID NO: 50

CMPRLRG-(D)-C;, SEQ ID NO: 51

(D)-CMPRLRG-(D)-C;, SEQ ID NO: 52

(D)-CMPRLRSarC;, SEQ ID NO: 53

(D)-CMPRKRGC;, SEQ ID NO: 54

(D)-CMPRLRCG;, SEQ ID NO: 55

(D)-CMPRLCRG;, SEQ ID NO: 56

(D)-CMPRCLRG;, SEQ ID NO: 57

CMPRGC;, SEQ ID NO: 58

PenMPRLRGC;, SEQ ID NO: 59

(D)-PenMPRLRGC;, SEQ ID NO: 60

(D)-CMPRLRGPen;, SEQ ID NO: 61

PenMPRLRGPen;, SEQ ID NO: 62

(D)-PenMPRLRGPen;, SEQ ID NO: 63

(D)-PenMPRLRG-(D)-Pen;, SEQ ID NO: 64

MpaMPRLRGC., SEQ ID NO: 65

As illustrated in the experimental section, these peptides bind LDLR without competition with LDL, exhibit high affinity and are capable of crossing the BBB and transporting molecules of interest.

In a particularly preferred embodiment, the peptides of formula (I) having a cyclic configuration are preferred. The peptide comprising sequence SEQ ID NO: 11, or a sequence derived therefrom, for example SEQ ID NO: 30 or SEQ ID NO: 48, is preferred in particular.

According to another embodiment, the peptides or pseudo-peptides of the invention are selected from the peptides of sequence SEQ ID NO: 12 to SEQ ID NO: 29 as follows:

MTVMPTGLWNPLIPS;, SEQ ID NO: 12

SASWFAVPIPPLRLE;, SEQ ID NO: 13

MTPMSTPRMLPVYVA;, SEQ ID NO: 14

MTATHLSTLFQPLTY;, SEQ ID NO: 15

MSPIPPAASTWANTL;, SEQ ID NO: 16

MTANPLQNAPGPLSL;, SEQ ID NO: 17

MQTAPPPPLTRVQWS;, SEQ ID NO: 18

GTPRMHIPLNVDHLP;, SEQ ID NO: 19

LTLPPISGLSSYPLP;, SEQ ID NO: 20

TPSAHAMALQSLSVG;, SEQ ID NO: 21

LTLPPISGLSSYPLP;, SEQ ID NO: 22

MGTLNAPTAYPQDSL;, SEQ ID NO: 23

LTNPPAYLPQNTDPH;, SEQ ID NO: 24

MGLPLPYIQTILHTP;, SEQ ID NO: 25

SAALIAMSSFKSITA;, SEQ ID NO: 26

SGFAFARSVPTESRR;, SEQ ID NO: 27

MTSPYMSLPPSTDDM;, SEQ ID NO: 28

LTNPPAYLPQNTDPH., SEQ ID NO: 29

As indicated above, the linear or cyclic peptides or pseudo-peptides of the invention can comprise peptide, non-peptide and/or modified peptide bonds. In a preferred embodiment, the peptides or pseudo-peptides comprise at least one peptidomimetic bond, chosen preferably among intercalation of a methylene ($-CH_2-$) or phosphate ($-PO_2-$) group, secondary amine ($-NH-$) or oxygen ($-O-$), alpha-azapeptides, alpha-alkylpeptides, N-alkylpeptides, phosphonamidates, depsipeptides, hydroxymethylenes, hydroxyethylenes, dihydroxyethylenes, hydroxyethylamines, retro-inverso peptides, methyleneoxy, cetomethylene, esters, phosphinates, phosphinics, phosphonamides and carba analogues.

Furthermore, in a particular embodiment, the peptides or pseudo-peptides of the invention comprise an N-term and/or C-term function protected, for example, by acylation, and/or amidation or esterification, respectively.

The peptides or pseudo-peptides of the invention can be synthesised by any technique known to the person skilled in the art (chemical, biological or genetic synthesis, etc.). They can be preserved as is, or be formulated in the presence of a substance of interest or any acceptable excipient.

For chemical syntheses, commercial equipment that can incorporate natural as well as non-natural amino acids, such as D-enantiomers and residues with side chains with hydrophobicities and steric hindrances different from those of their natural homologues (so-called exotic, i.e., non-coded, amino acids), or a peptide sequence containing one or more peptidomimetic bonds that can include notably intercalation of a methylene ($-CH_2-$) or phosphate ($-PO_2-$) group, a secondary amine ($-NH-$) or an oxygen ($-O-$), is used.

During synthesis, it is possible to introduce various chemical modifications, such as for example, coupling in the N-term or C-term position or on a side chain a lipid (or phospholipid) derivative or a constituent of a nanoparticle, in order to be able to incorporate the peptide or pseudo-peptide of the invention within a lipid membrane such as that of a liposome composed of one or more lipid layers or bilayers, or of a nanoparticle.

The peptides of the invention, or a protein part thereof, can also be obtained from a nucleic acid sequence coding for same. The present invention also relates to a nucleic acid molecule comprising, or constituted by, a nucleic sequence coding for a peptide such as defined above. More particularly, the invention relates to a nucleic acid molecule comprising at least one sequence coding for a compound of general formula (I) or corresponding to one of the sequences SEQ ID NO: 12 to SEQ ID NO: 29 or a protein part thereof. These nucleic acid sequences can be DNA or RNA and be combined with control sequences and/or be inserted in biological expression vectors.

The biological expression vector used is selected according to the host in which it will be transferred. It can be, for example, a plasmid, cosmid, virus, etc. The invention relates in particular to these nucleic acids and biological expression vectors, which can be used to produce the peptides of the invention, or protein parts thereof, in a host cell. These biological expression vectors can be prepared and the peptides can be produced or expressed in a host by molecular biology and genetic engineering techniques well known to the person skilled in the art.

As indicated, the peptides of the invention are particularly useful for formulating substances of therapeutic or diagnostic interest, and notably to promote the biodistribution and/or passage thereof across the BBB.

In this respect, the invention relates to the use of a linear or cyclic peptide or pseudo-peptide such as defined above as a vector for the transfer/transport of molecules of therapeutic interest, or imaging or diagnostic agents, or any other molecule.

The invention also relates to the use of a linear or cyclic peptide or pseudo-peptide such as defined above for preparing a drug capable of crossing the BBB.

The invention also relates to a method for enabling or improving the passage of a molecule across the BBB, comprising the coupling of the molecule to a peptide or pseudo-peptide of the invention.

The linear or cyclic peptides or pseudo-peptides of the invention make it possible to cross the BBB with an active substance that normally can cross this barrier only little or not at all. They can thus be used in the treatment, prevention or diagnosis of any disease affecting the CNS, but also as transporters of biological material (biotransporters) in the context of studies undertaken on various families of molecules with cell membrane models and more particularly BBB models.

In this respect, the present application describes various prodrug conjugate compounds comprising a peptide or pseudo-peptide such as defined above. The term "conjugate" designates a molecule resulting from the combination between one or more of the peptides or pseudo-peptides of the invention and one or more molecules of interest. As will be described in further detail below, conjugation can be of chemical nature, as by means of a linker or spacer, or of genetic nature, such as, for example, genetic recombination technology, such as in a fusion protein with, for example, a marker or tracer molecule (for example, GFP, β-galactosidase, etc.) or a therapeutic molecule (for example, growth factor, neurotrophic factor, etc.).

Thus, the invention relates in particular to a conjugate compound of formula (II) as follows:

$$VxDy \qquad \text{(II)}$$

wherein V represents a linear or cyclic peptide or pseudo-peptide of the invention, D represents an active substance or substance of interest, and x and y are integers between 1 and 5. In a particular embodiment, x and y are equal to 1, or x is greater than y.

As an example, the conjugate wherein V=cMPRLRGC, x=1, D=Y-(D)-AGFLR and y=1 was synthesised. In this case, the active substance is an analgesic therapeutic peptide, dalargin. Direct coupling (synthesis in tandem) of this therapeutic peptide at the N-term of peptide vector SEQ ID NO: 48 gives the conjugate SEQ ID NO: 66, Y-(D)-AGFLR-(D)-CMPRLRGC.

The invention also relates to a conjugate compound of formula (III) as follows:

$$VxLzDy \qquad \text{(III)}$$

wherein V represents a linear or cyclic peptide or pseudo-peptide of the invention, L represents a spacer (or linker), D represents an active substance or substance of interest, x and y are integers between 1 and 5 and z is an integer between 1 and 10. In a particular embodiment, x=z=y=1 or x=z>y or z>x>y.

As an example, conjugates wherein V=cMPRLRGC (with x=1) and D=Y-(D)-AGFLR (with y=1) were synthesised via linkers with L=GGG or GFLG or ALAL or β-Ala or Ahx or GFAL (with z=1).

```
                                          SEQ ID NO: 67
Y-(D)-AGFLRGGG-(D)-CMPRLRGC,

SEQ ID NO: 68
Y-(D)-AGFLRGFLG-(D)-CMPRLRGC,

SEQ ID NO: 69
Y-(D)-AGFLRALAL-(D)-CMPRLRGC,

SEQ ID NO: 70
Y-(D)-AGFLR-β-Ala-(D)-CMPRLRGC,

SEQ ID NO: 71
Y-(D)-AGFLR-Ahx-(D)-CMPRLRGC,

SEQ ID NO: 72
Y-(D)-AGFLRGFAL-(D)-CMPRLRGC,
```

The examples contained in the present application show, in brain perfusion experiments in the mouse, that these conjugates are capable of crossing the BBB, illustrating the mechanism of action of the peptide vectors of the invention.

The active substance or substance of interest can be any molecule of pharmaceutical interest, notably therapeutic, a diagnostic or medical imaging agent, or a molecular probe. It can be in particular any chemical entity of biological interest such as a small chemical molecule (antibiotic, antiviral, immunomodulator, antineoplastic, anti-inflammatory, etc.), a peptide or polypeptide, a protein (enzyme, hormone, cytokine, apolipoprotein, growth factor, antigen, antibody or part of an antibody), a nucleic acid (ribonucleic acid or deoxyribonucleic acid of human, viral, animal, eukaryotic or prokaryotic, plant or synthetic origin, etc., whose size can range from that of a single oligonucleotide to that of the genome or a genome fragment), a viral genome or a plasmid, a ribozyme, a marker or a tracer. Generally, the "substance of interest" can be any active pharmaceutical ingredient (API), whether a chemical, biochemical, natural or synthetic compound. The expression "small chemical molecule" designates a molecule of pharmaceutical interest with a maximum molecular weight of 1000 Daltons, typically between 300 Daltons and 700 Daltons.

The invention also relates to a compound of the following formula (IV):

$$VxLz \qquad (IV)$$

wherein V represents a linear or cyclic peptide or pseudo-peptide of the invention, L represents a spacer (or linker), x is an integer between 1 and 5 and z is an integer between 1 and 10. In a particular embodiment, x=z=1 or z>x.

In the conjugate compounds of the invention, coupling between V and D, or between V and L on the one hand and L and D on the other hand, can be carried out by any acceptable means of bonding taking into account the chemical nature, hindrance and number of associated active substances and peptides or pseudo-peptides. Coupling can thus be carried out by one or more covalent, hydrophobic or ionic bonds, cleavable or non-cleavable in physiological medium or within cells. Furthermore, D can be coupled with V, if need be via L, at various reactive groups, and notably at one or more N-term and/or C-term ends of V and/or at one or more reactive groups carried by the natural or non-natural amino acid side chains constitutive of V.

Coupling can be carried out at any site of the peptide or pseudo-peptide where functional groups such as —OH, —SH, —CO$_2$H, —NH$_2$, —SO$_3$H or —PO$_2$H are naturally present or have been introduced. Thus, a therapeutic molecule of interest, or a diagnostic (or medical imaging) agent or any other molecule such as a molecular probe can be linked (coupled) to the linear or cyclic peptide or pseudo-peptide vector of the invention by a covalent bond either at the N-term or C-term ends, or at the reactive groups carried by the natural or non-natural amino acid side chains of this peptide sequence.

Similarly, coupling can be carried out at any site of the active substance or substance of interest (molecule of therapeutic interest, diagnostic or medical imaging agent, any other molecule such as a molecular probe) where, for example, functional groups such as —OH, —SH, —CO$_2$H, —NH$_2$, —SO$_3$H, —PO$_2$H are naturally present or have been introduced.

It is preferable that the interaction is sufficiently strong so that the peptide is not dissociated from the active substance before having reached its site of action. For this reason, the preferred coupling of the invention is covalent coupling, but non-covalent coupling could be used, however. The substance of interest can be coupled directly with the peptide (synthesis in tandem) either at one of these terminal ends (N-term or C-term), or at a side chain of one of the constitutive amino acids of the sequence (FIG. 2). The substance of interest can also be coupled indirectly by means of a linker or spacer, either at one of the terminal ends of the peptides, or at a side chain of one of the constitutive amino acids of the sequence (FIG. 2). Means of covalent chemical coupling, calling upon a spacer or not, include those selected from bi- or multifunctional agents containing alkyl, aryl or peptide groups by esters, aldehydes or alkyl or aryl acids, anhydride, sulfhydryl or carboxyl groups, groups derived from cyanogen bromide or chloride, carbonyldiimidazole, succinimide esters or sulphonic halides.

In this respect, the invention also relates to a method for preparing a conjugate compound such as defined above, characterised in that it comprises a step of coupling between a peptide or pseudo-peptide V and a substance D, if need be via L, preferably by a chemical, biochemical or enzymatic pathway, or by genetic engineering.

The invention also relates to a pharmaceutical composition characterised in that it comprises at least one conjugate compound such as defined above and one or more pharmaceutically acceptable excipients.

The invention also relates to a diagnostic composition characterised in that it comprises a diagnostic or medical imaging agent composed of a conjugate compound such as defined above.

The conjugate can be used in the form of any pharmaceutically acceptable salt. The expression "pharmaceutically acceptable salts" refers to, for example and in a non-restrictive way, pharmaceutically acceptable base or acid addition salts, hydrates, esters, solvates, precursors, metabolites or stereoisomers, said vectors or conjugates loaded with at least one substance of interest.

The expression "pharmaceutically acceptable salts" refers to nontoxic salts, which can be generally prepared by reacting a free base with a suitable organic or inorganic acid. These salts preserve the biological efficacy and the properties of free bases. Representative examples of such salts include water-soluble and water-insoluble salts such as acetates, N-methylglucamine ammonium, amsonates (4,4-diaminostilbene-2,2'-disulphonates), benzenesulphonates, benzonates, bicarbonates, bisulphates, bitartrates, borates, hydrobromides, bromides, buryrates, camsylates, carbonates, hydrochlorates, chlorides, citrates, clavulanates, dichlorhydrates, diphosphates, edetates, calcium edetates, edisylates, estolates, esylates, fumarates, gluceptates, gluconates, glutamates, glycolylarsanylates, hexafluorophosphates, hexylresorcinates, hydrabamines, hydroxynaphthoates, iodides, isothionates, lactates, lactobionates, laurates, malates, maleates, mandelates, mesylates, methylbromides, methylnitrates, methylsulphates, mucates, napsylates, nitrates, 3-hydroxy-2-naphthoates, oleates, oxalates, palmitates, pamoates (1,1-methylene-bis-2-hydroxy-3-naphtoates, or emboates), pantothenates, phosphates, picrates, polygalacturonates, propionates, p-toluenesulphonates, salicylates, stearates, subacetates, succinates, sulphates, sulphosalicylates, suramates, tannates, tartrates, teoclates, tosylates, triethiodides, trifluoroacetates and valerianates.

The compositions of the invention advantageously comprise a pharmaceutically acceptable vehicle or excipient. The pharmaceutically acceptable vehicle can be selected from the vehicles classically used according to each mode of administration. According to the mode of administration envisaged, the compounds can be in solid, semi-solid or liquid form. For solid compositions such as tablets, pills, powders, or granules that are free or are included in gelatin capsules, the active substance can be combined with: a) diluents, for example lactose, dextrose, sucrose, mannitol, sorbitol, cellulose and/or glycine; b) lubricants, for example silica, talc, stearic acid, its magnesium or calcium salt and/or polyethylene glycol; c) binders, for example magnesium and aluminium silicate, starch paste, gelatin, tragacanth, methylcellulose, sodium carboxymethyl cellulose and/or polyvinylpyrrolidone; d) disintegrants, for example starch, agar, alginic acid or its sodium salt, or effervescent mixtures; and/or e) absorbents, dyes, flavouring agents and sweeteners. The excipients can be, for example, mannitol, lactose, starch, magnesium stearate, sodium saccharin, talc, cellulose, glucose, sucrose, magnesium carbonate and analogues of pharmaceutical quality. For semi-solid compositions such as suppositories, the excipient can, for example, be an emulsion or oily suspension, or polyalkylene glycol-based, such as polypropylene glycol. Liquid compositions, in particular injectables or those included in a soft capsule, can be prepared, for example, by dissolution, dispersion, etc., of the active substance in a pharmaceutically pure solvent such as, for example, water, physiological saline solution, aqueous dextrose, glycerol, ethanol, oil and analogues thereof.

The compositions or conjugates of the invention can be administered by any suitable route and, in a non-restrictive way, by parenteral route, such as, for example, in the form of preparations that can be injected by subcutaneous, intravenous or intramuscular route; by oral route (or per os), such as, for example, in the form of coated or uncoated tablets, gelatin capsules, powders, pellets, suspensions or oral solutions (one such form for oral administration can be either with immediate release or with extended or delayed release); by rectal route such as, for example, in the form of suppositories; by topical route, in particular by transdermal route, such as, for example, in the form of patches, pomades or gels; by intranasal route such as, for example, in aerosol and spray form; by perlingual route; or by intraocular route.

The pharmaceutical compositions typically comprise an effective dose of a peptide or pseudo-peptide or conjugate of the invention. A "therapeutically effective dose" as described herein refers to the dose that gives a therapeutic effect for a given condition and administration schedule. It is typically the average dose of an active substance to administer to appreciably improve some of the symptoms associated with a disease or a pathological state. For example, in treating a cancer of the brain or of other tissue/organ, a pathology, a lesion or a disorder of the CNS, the dose of an active substance that decreases, prevents, delays, eliminates or stops one of the causes or symptoms of the disease or disorder would be therapeutically effective.

A "therapeutically effective dose" of an active substance does not necessarily cure a disease or disorder but will provide a treatment for this disease or disorder so that its appearance is delayed, impeded or prevented, or its symptoms are attenuated, or its term is modified or, for example, is less severe, or the recovery of the patient is accelerated.

It is understood that the "therapeutically effective dose" for a person in particular will depend on various factors, including the activity/efficacy of the active substance, its time of administration, its route of administration, its rate of elimination and metabolism, drug combinations/interactions and the severity of the disease (or disorder) treated on a preventive or curative basis, as well as the age, weight, overall health, sex and/or diet of the patient.

Depending on the substance coupled, the conjugates and compositions of the invention can be used for treating, preventing, diagnosing or imaging numerous pathologies, notably pathologies affecting the CNS, infectious pathologies or cancers.

In this respect, the invention relates to the use of pharmaceutical conjugates or compositions as described above for treating or preventing CNS pathologies or disorders, brain tumours or other cancer cells, and bacterial, viral, parasitic or fungal infectious pathologies of the brain or other tissues/organs.

The invention also relates to the use of conjugates or pharmaceutical compositions as described above for diagnosing or imaging CNS pathologies or disorders, brain tumours or other cancer cells, and bacterial, viral, parasitic or fungal infectious pathologies of the brain or other tissues/organs.

The invention also relates to the use of a conjugate or composition such as defined above for treating, imaging and/ or diagnosing a brain tumour or other types of cancer cells. Studies have indeed shown that patients with some cancers have hypocholesterolemia. This hypocholesterolemia is the consequence of an overuse of cholesterol by cancer cells. The latter to survive induce an increase in the level of LDLR expression within organs with tumours (Henricksson et al., 1989, *Lancet*, 2(8673), 1178-1180). There is thus a correlation between the increase in the level of LDLR expression by cells and some cancers. It has also been recently shown that the number of LDLR is very high on the surface of some pathological cells such as cancer cells. It is generally accepted that 1,000 to 3,000 LDLR are present at the surface of a non-pathological cell. Similarly, non-pathological neurons have only few LDLR (Pitas et al., 1987, *J. Biol. Chem.*, 262, 14352-14360). In the case of the glioblastoma, LDLR overexpression has been shown. Thus, on the surface of brain tumour cells, 125,000 (for U-251 cells) to 900,000 (for SF-767 cells) LDLR have been counted (Malentiska et al., 2000, *Cancer Res.*, 60, 2300-2303; Nikanjam et al., 2007, *Int. J. Pharm.*, 328, 86-94). It should also be noted that many tumour cells overexpress LDLR, such as those of prostate cancer (Chen et al., 2001, *Int. J. Cancer*, 91, 41-45), colon cancer (Niendorf et al., 1995, *Int. J. Cancer*, 61, 461-464), leukaemia (Tatidis et al., 2002, *Biochem. Pharmacol.*, 63, 2169-2180), colorectal cancer (Caruso et al., 2001, *Anticancer Res.*, 21, 429-433), breast cancer (Graziani et al., 2002, *Gynecol. Oncol.*, 85, 493-497), as well as cancers of the liver, pancreas, ovaries, lung and stomach, etc.

The invention also relates to the use of a conjugate or composition such as defined above for treating, imaging and/ or diagnosing bacterial, viral, parasitic or fungal infectious pathologies of the brain or other tissues/organs, such as, and in a non-restrictive way, AIDS or meningitis, etc. LDLR is also present on hepatic cells. It is now known that endocytosis of the hepatitis C virus (HCV) can occur via LDLR. LDLR could serve as a viral receptor at an early stage of infection of human hepatocytes by HCV (Molina et al., 2007, *J. Hepatol.*, 46(3), 411-419). The conjugates of the invention can thus be used to specifically target pathological cells, infected by viruses such as those of hepatitis B and hepatitis C that express LDLR and/or to modulate via LDLR the viral infection process of healthy cells.

The invention also relates to the use of a conjugate or composition such as defined above for treating, imaging and/ or diagnosing neurodegenerative pathologies such as, in a non-restrictive manner, Alzheimer's disease, Parkinson's disease, Creutzfeldt-Jakob disease, stroke/cerebrovascular accidents (CVA), bovine spongiform encephalopathy, multiple sclerosis, amyotrophic lateral sclerosis, etc.

The invention also relates to the use of a conjugate or composition such as defined above for treating, imaging and/ or diagnosing neurological pathologies such as, in a non-restrictive manner, epilepsy, migraine, encephalitis, CNS pain, etc.

The invention also relates to the use of a conjugate or composition such as defined above for treating, imaging and/ or diagnosing neuropsychiatric pathologies such as, in a non-restrictive manner, depression, autism, anxiety, schizophrenia, etc.

The terms "treatment," "treating," "treat" and other similar expressions refer to obtaining a pharmacological and/or physiological effect, for example, inhibition of cancer cell growth, cancer cell death or improvement of a disease or neurological disorder. The effect can be prophylactic or preventive in order to completely or partially prevent the aggravation of a disease or a symptom such a disease, in an ill person, or its propagation, in healthy subjects, and/or can be therapeutic in order to completely or partially treat a disease and/or its related harmful effects. The term "treatment" as used in the present document covers any treatment of a disease in a mammal, and more particularly in man, and comprises: (a) prevention of a disease (for example, prevention of cancer) or a condition that can arise in a person predisposed to this pathology or disorder, but who has not yet been positively diagnosed, (b) the slowing down of a disease (for example, by stopping its development), or (c) relief from a disease (for example, by reducing the symptoms associated with a disease). This term "treatment" also covers any administration of an active substance in order to tend, cure, relieve, improve, decrease or inhibit a condition in an individual or patient, including, but not limited to, the administration to a person in need of a drug composed of a vector or conjugate as described in the present document.

The present invention also relates to the use of a linear or cyclic peptide or pseudo-peptide of the invention to increase the biological activity of an active substance or a substance of interest (therapeutic molecule of interest, diagnostic or medical imaging agent, or any other molecule such as a molecular probe) to which it is coupled.

The present invention also relates to the use of a linear or cyclic peptide or pseudo-peptide of the invention to decrease the toxicity of the active substance or substance of interest (therapeutic molecule of interest, diagnostic or medical imaging agent, or any other molecule such as a molecular probe) to which it is coupled.

Other aspects and advantages of the present invention will become apparent upon consideration of the examples below, which are only illustrative in nature and which do not limit the scope of the present application.

EXAMPLES

Example I

Cloning of human and murine LDLR in an expression vector.

Peptides were identified on the basis of their interaction with and affinity for human and murine low-density lipoprotein receptors (hLDLR and mLDLR), which are notably involved in the endocytosis and transcytosis (transcellular transport, notably across the BBB) of cholesterol. The precondition to the characterisation of these peptides was the establishment in eukaryotic cells (Chinese hamster ovary cells, CHO) of stable cell lines expressing hLDLR and mLDLR constitutively and at high rates. These cell lines are used: i) for the characterisation of peptides binding to hLDLR expressed at the cell surface, in its native configuration; and ii) to verify that hLDLR and mLDLR can internalise the selected peptides by endocytosis.

The construction of these cell lines is briefly described.

The messenger RNA sequences coding for hLDLR and mLDLR are available in databases (accession numbers: NM_000527 and NM_010700, respectively). The primers necessary for cDNA amplification by PCR were selected, comprising at their end (in bold type) the restriction sites necessary (HindIII and SalI for human LDLR and HindIII and KpnI for murine LDLR) for cloning in the pEGFP-N1 expression vector (Clontech):

```
hLDLR
Forward primer:
                                (SEQ ID NO: 75)
ATATATAAGCTTCGAGGACACAGCAGGTCGTGAT Reverse primer:
                                (SEQ ID NO: 76)
TTAATTGTCGACCACGCCACGTCATCCTCCAGACT mLDLR
```

```
                          -continued
Forward primer:
                                (SEQ ID NO: 77)
ATATATAAGCTTGACGCAACGCAGAAGCTAAG Reverse primer:
                                (SEQ ID NO: 78)
TTAATTGGTACCGTTGCCACATCGTCCTCCAG
```

Figure 3:
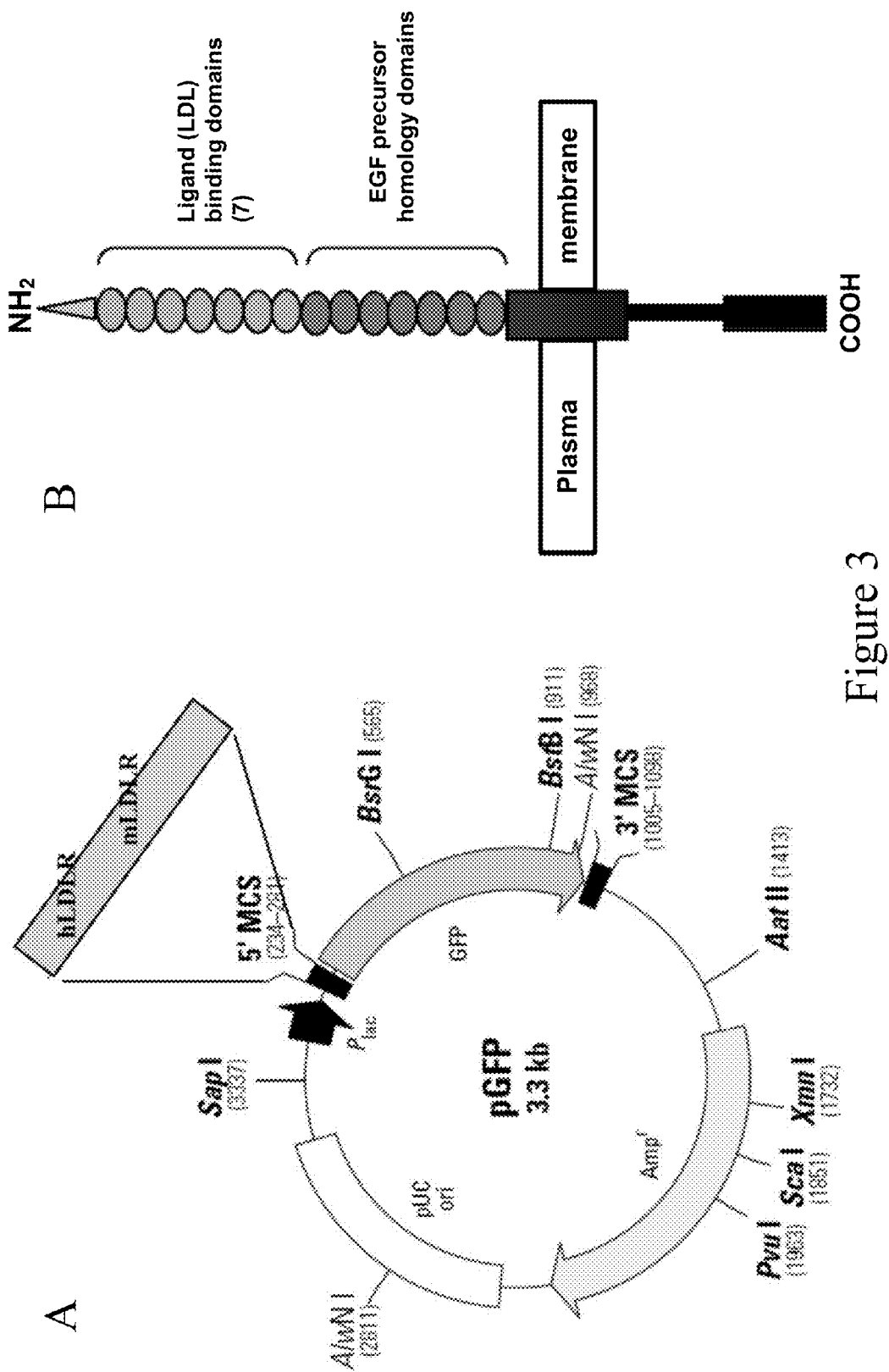

Total RNA prepared from human and murine brains were transformed into cDNA by reverse transcription for PCR amplification of DNA fragments coding for hLDLR and mLDLR. After amplification, the PCR products were digested by HindIII-SalI and HindIII-KpnI restriction enzymes, respectively, and ligated in the pEGFP-N1 expression vector (Clontech), digested by the same restriction enzymes. After transfection in eukaryotic cells, this vector enables the expression, under control of the CMV promoter, of LDLR fused with GFP at their C-term end, i.e., at the end of their intracellular domains (FIG. 3). After transforming competent E. coli DH5α bacteria, obtaining isolated colonies and preparing plasmid DNA, both strands of the constructions were sequenced in their entirety for verification.

Example II

Establishment of CHO cell lines stably expressing human and murine LDLR.

Figure 4:
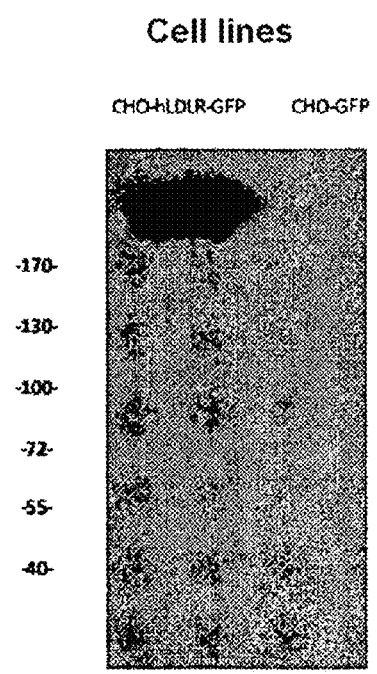

Transitory transfections in various cell lines (CHO, COS, N2A and HEK293) were carried out to determine on living or fixed cells the expression levels and membrane location of hLDLR and mLDLR. The receptor is directly visible on living cells, under fluorescence microscopy, without the need for immunostaining, by virtue of green fluorescence emitted by GFP fused at the C-term of these receptors. Stable transfectants were selected by limit dilution and by the geneticin resistance gene (G418) carried by the expression vector. These cell lines were amplified while maintaining selective pressure. In the example cited here, the expression of hLDLR-GFP of the expected size was verified by Western blot on cell lysates with antibodies directed against human LDLR and against GFP. A protein corresponding to the combined sizes of GFP and hLDLR (190 kDa) is recognised by anti-hLDLR (FIG. 4) and anti-GFP antibodies in cell extracts prepared from stable cell lines. A CHO cell line expressing GFP constitutively was used as negative control. The anti-hLDLR antibody detects no protein in the GFP cell line.

Figure 5:
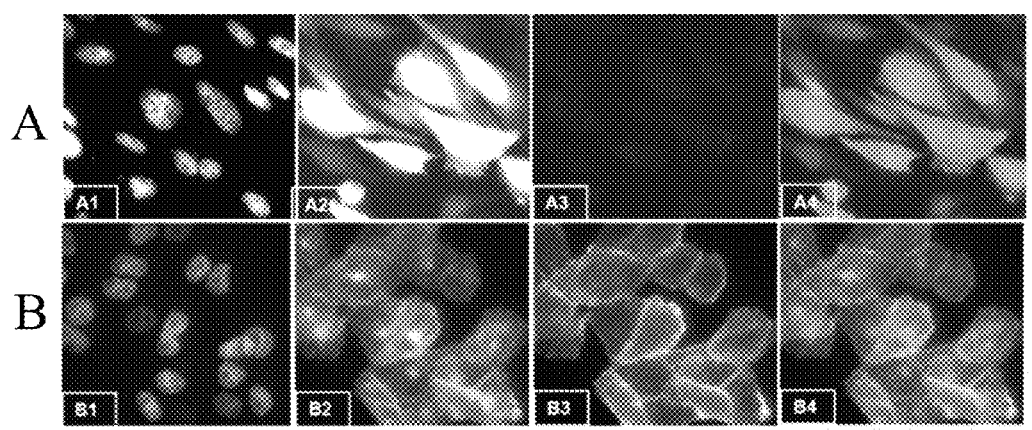

Immunocytochemistry with anti-hLDLR antibody on fixed (PFA) cells of the CHO-GFP (control) and CHO-hLDLR-GFP cell lines shows that hLDLR-GFP fusion is well expressed in the transfected cells. Immunocytochemistry experiments on non-permeabilised cells with Triton X100 show that the extracellular domain of LDLR is well detected at the extracellular level (FIG. 5).

Figure 6:
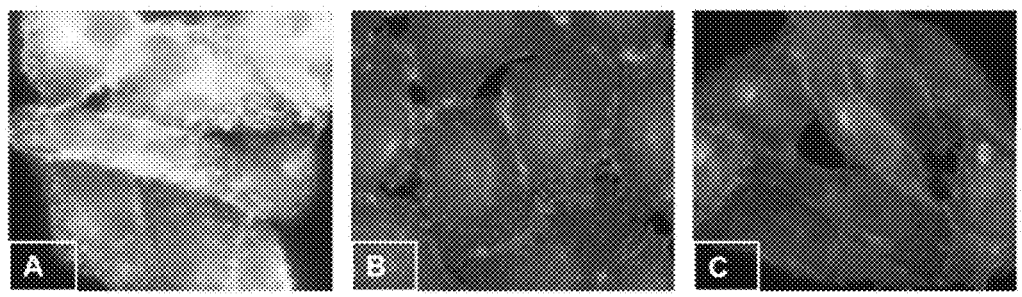

Co-location between hLDLR and its natural ligand LDL, made fluorescent by adsorption of DiI, a fluorescent marker, is shown. This natural fluorescent ligand (DiI-LDL) is quickly is internalised (endocytosis) as visualised under fluorescence microscopy on fixed cells (FIG. 6-A). In contrast, DiI-LDL is not incorporated by endocytosis by the control CHO-GFP cell line, or by another control CHO cell line, which overexpresses, for example, human transferrin receptor (hTfR, FIG. 6-B), another receptor involved in transcytosis. Moreover, endocytosis activity of the CHO-LDLR-GFP cell line is specific to the LDLR ligand since in this cell line endocytosis of ligands not specific for it, for example transferrin (TO stained with red fluorochrome (Texas Red, FIG. 6-C), is not observed.

Receptor functionality (endocytosis capacity) is confirmed by real-time experiments, under video fluorescence microscopy showing that LDL, natural ligand of hLDLR, stained with DiI, is actually transported rapidly and very effectively in cells expressing hLDLR-GFP compared with cells expressing GFP alone or cells expressing another receptor involved in endocytosis such as hTfR (negative control). Conversely, video microscopy experiments carried out with Tf stained with Texas Red, which is very efficiently incorporated by endocytosis by cells expressing hTfR-GFP, confirm that transferrin is not incorporated by endocytosis by cells of a control GFP cell line or by cells of an hLDLR cell line.

In spite of a high hLDLR expression level in CHO-hLDLR-GFP cell lines, the endocytosis system is not only effective, but it preserved its selectivity. The presence of GFP fusion altered neither the membrane insertion properties of hLDLR, exposure outside the cell of the hLDLR extracellular domain, nor the functionality of the receptor in endocytosis processes.

Example III

Screening of databases of several billion random peptide sequences expressed by bacterial viruses on CHO-hLDLR-GFP cell lines and identification of bacterial viruses and thus peptide sequences exhibiting an affinity for hLDLR.

Screening with databases of random peptide sequences expressed by bacterial viruses was used on the CHO-hLDLR-GFP cell line, after exhaustion of bacterial virus databases on a control CHO-GFP cell line expressing GFP alone. After abundant washing and then elution with acid, the bacterial viruses fixed on the cell lines are amplified by infection of *E. coli* ER 2738 bacteria in liquid medium or on Petri dishes. Reiterative screening on cell lines of bacterial viruses eluted and then reamplified enabled the characterisation of bacterial viruses exhibiting strong affinity for hLDLR expressed at the cell surface. Among these bacterial viruses, only those which also bind to the murine cell line (CHO-mLDLR-GFP) were selected.

Five independent screenings were carried out and in total roughly 200 bacterial virus clones (delayed plaques) were sequenced after PCR amplification of regions of the bacterial virus genome coding for the peptides expressed by these bacterial viruses. Numerous bacterial viruses had identical sequences. Two peptide sequence families were obtained: conserved-motif cyclic peptides, SEQ ID NO: 1 to SEQ ID NO: 11 and SEQ ID NO: 30 to SEQ ID NO: 65, and linear peptides with no conserved motif, SEQ ID NO: 12 to SEQ ID NO: 29 (see the sequence lists of the present document).

Figure 7:
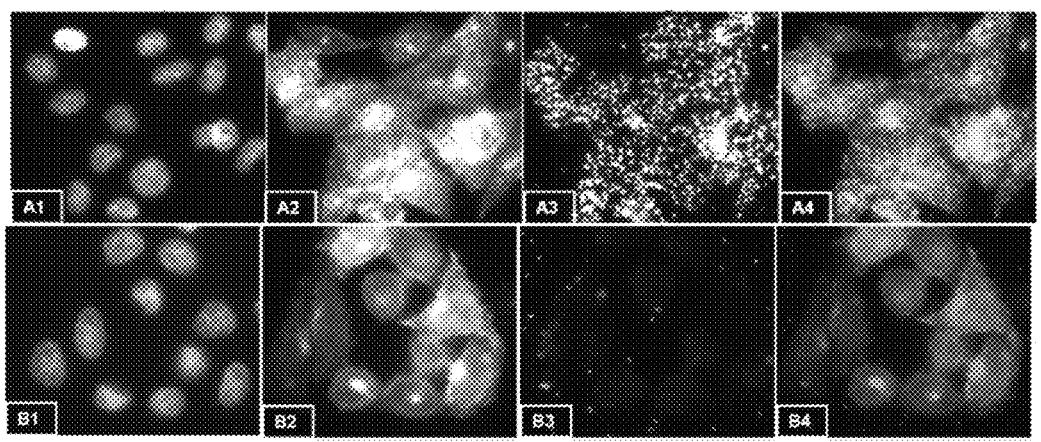

The bacterial virus clones identified following the binding of the peptides, which they express and which bind to hLDLR-GFP expressed by the stable CHO-hLDLR-GFP cell line, were brought together with LDLR cells and, after intensive washing, were detected with an antibody directed against the viral envelope protein of the bacterial virus followed by a second antibody coupled with Alexa 594 (FIG. 7). These bacterial viruses do not bind to cells of the control CHO-GFP cell line expressing GFP alone.

Batches of purified bacterial viruses with identical titres were put in competition on cell lines and after intensive washing and elution with acid, cloning and sequencing of roughly 50 bacterial viruses, those with the highest affinities among the cyclic and linear peptides were identified.

Those not selected or retained for other experiments are in no case considered of no use; they cannot be regarded as nonfunctional. These peptides preserve great potential as vector candidates and, as a consequence, they also are claimed by the present invention.

Example IV

Interaction of peptides expressed by bacterial viruses with hLDLR of CHO-LDLR-GFP cell lines and with hLDLR of non-genetically modified cells.

Figure 8:
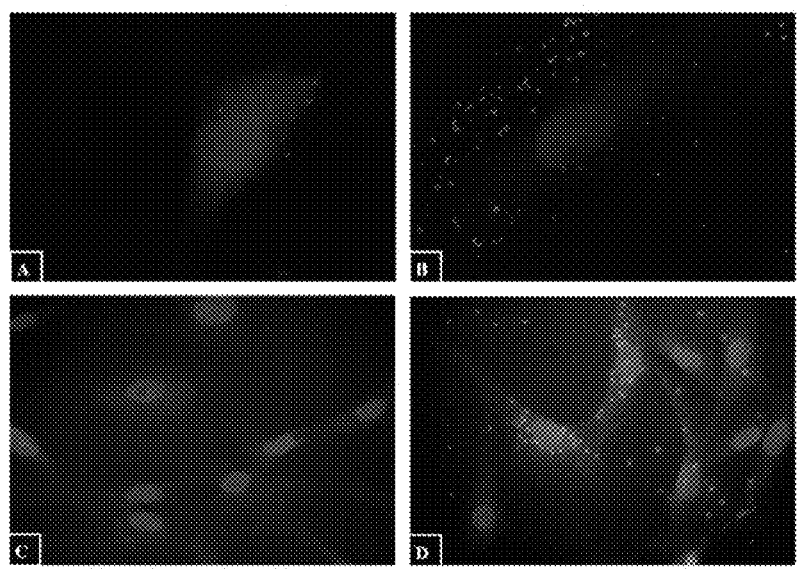

The bacterial viruses expressing peptides with affinity for hLDLR were incubated with adherent cells, non-genetically modified, known to express hLDLR in a constitutive or inducible way, notably human fibroblasts, human umbilical vein endothelial cells (HUVEC) or porcine brain microvascular endothelial cells. Immunocytochemistry with antibodies directed against the viral envelope protein of the bacterial virus show that peptides with affinity for hLDLR, expressed by bacterial viruses, also bind to LDLR present on primary cells, non-genetically modified, for example human fibroblasts and porcine brain microvascular endothelial cells (FIG. 8).

Qualitative immunocytochemistry was supplemented with quantitative flow cytometry (FACS) with suspended cells (GFP cell line, CHO-hLDLR-GFP cell line, human fibroblasts, HUVEC). These cells were grown in culture medium, mechanically unbound and dissociated (without trypsin), centrifuged, resuspended and incubated in the presence of various bacterial virus clones and anti-LDLR antibody, for 20 min at 4° C. in order to avoid any process of endocytosis. After washings, the bacterial viruses bound to cells were visualised with anti-viral envelope protein antibody. FACS analyses were carried out with a FACSCanto system (Becton Dickinson) using BD FACSDiva software. The number of positive cells was standardised with 5,000 events for each test. The results were expressed in arbitrary units of fluorescence.

Figure 9:
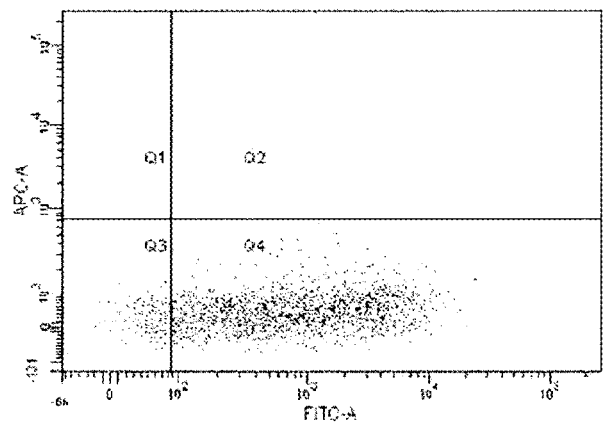
Figure 9:
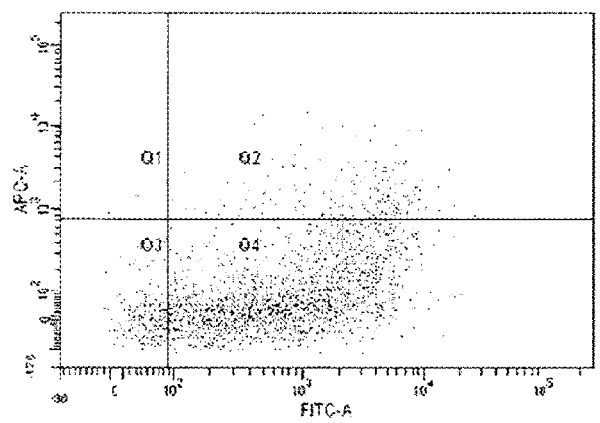
Figure 9:
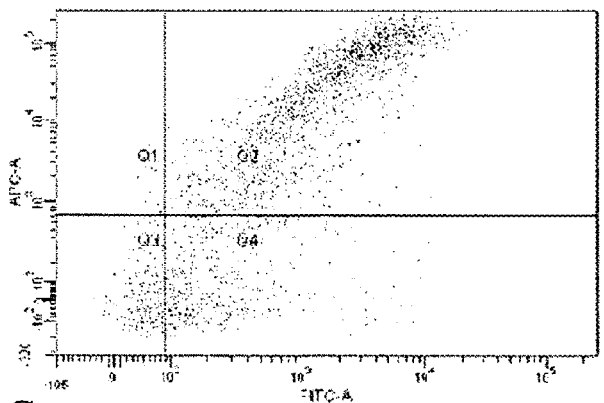
Figure 10:
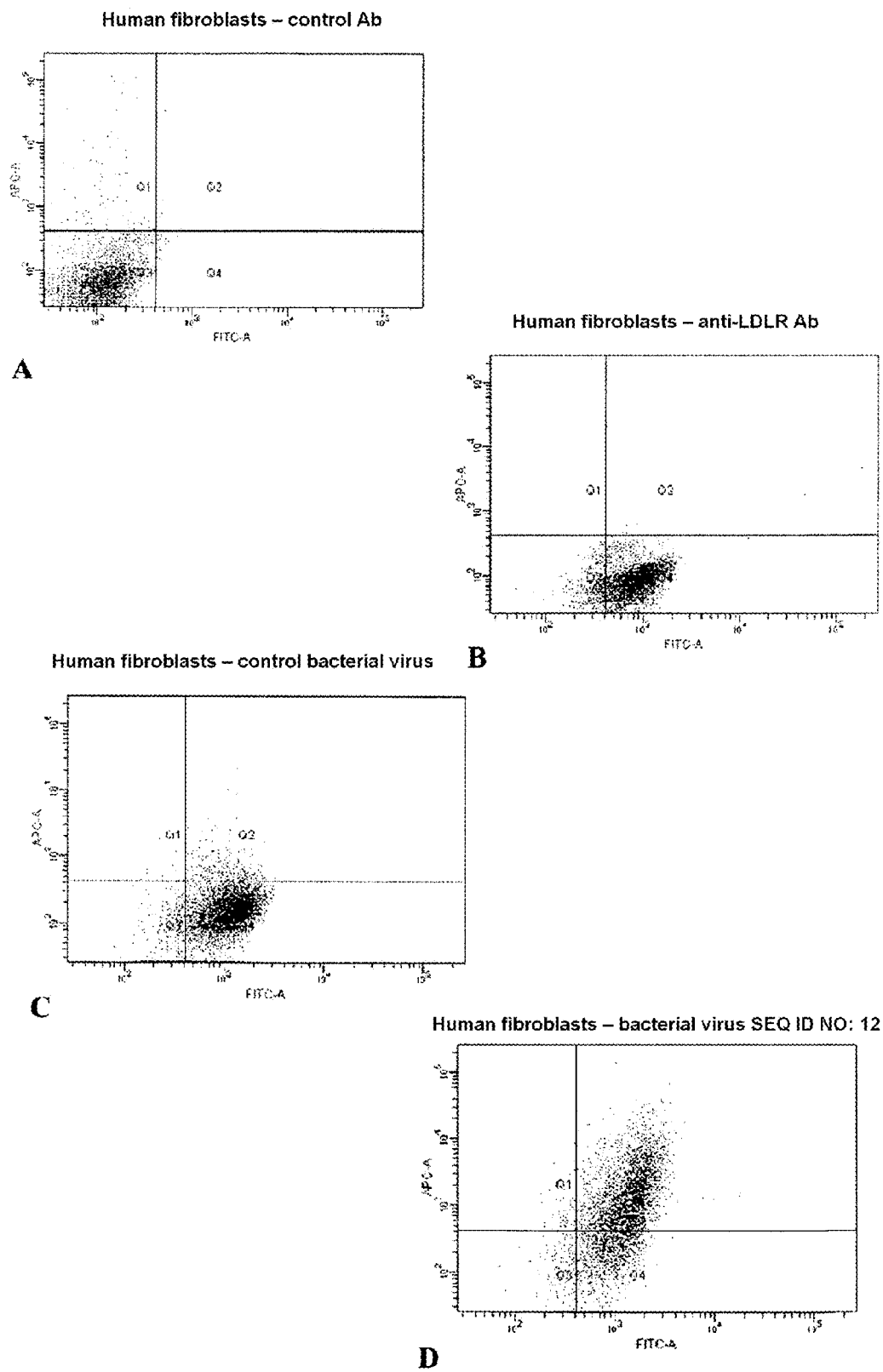
Figure 11:
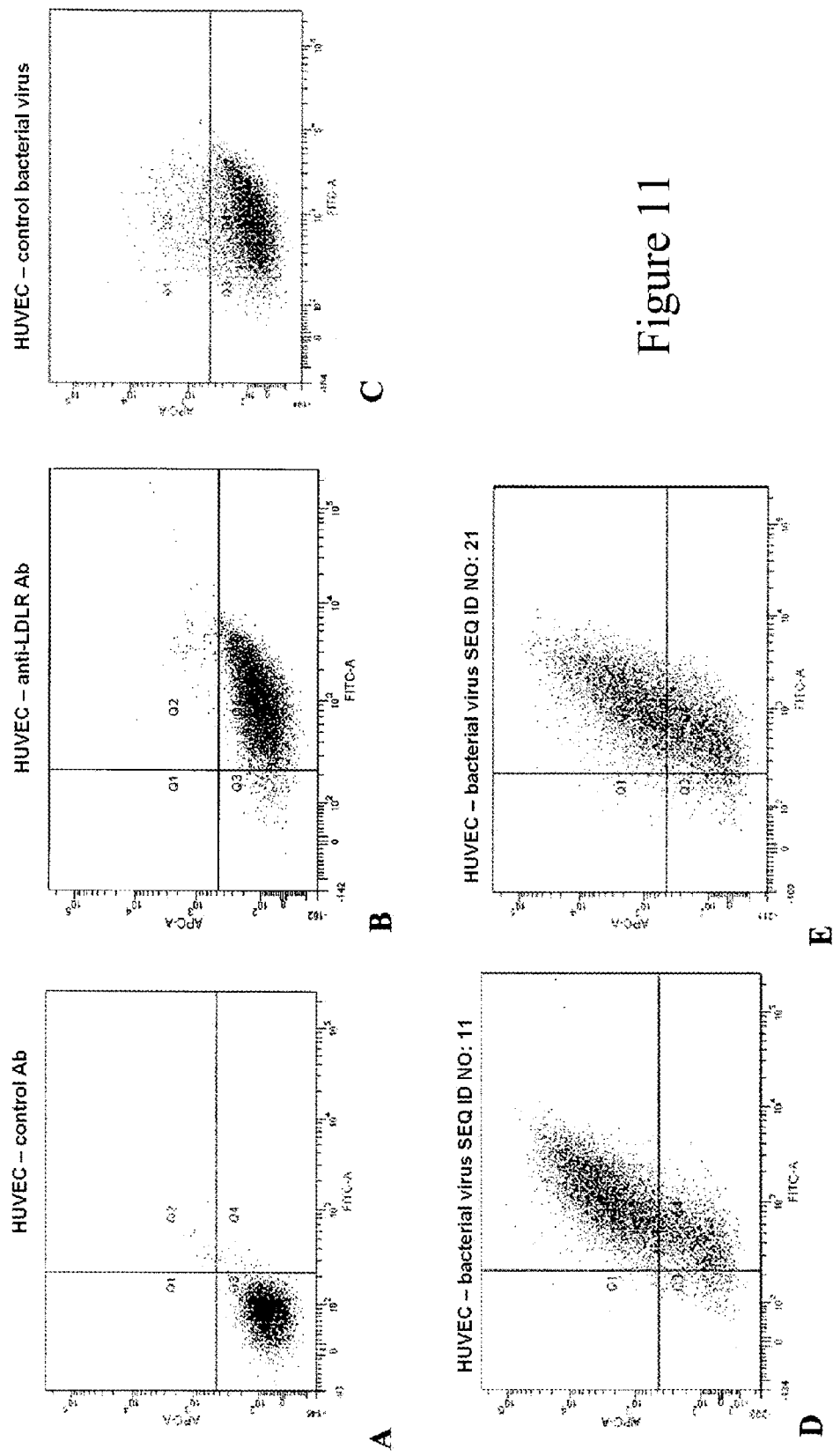

These approaches showed a correlation between hLDLR expression rate determined by anti-hLDLR antibody visualised by secondary antibody Alexa 488 (horizontal axis) on various cell types (FIGS. 9-11), and an antibody directed against bacterial virus envelope protein visualised by Alexa 647 antibody or allophycocyanine (APC) antibody (vertical axis). FIGS. 9, 10, 11 correspond to the results obtained for peptides SEQ ID NO: 11, SEQ ID NO: 12 and SEQ ID NO: 21 on cells of the CHO-hLDLR-GFP cell line (FIG. 9), human fibroblasts (FIG. 10) and HUVEC (FIG. 11).

Figure 12:
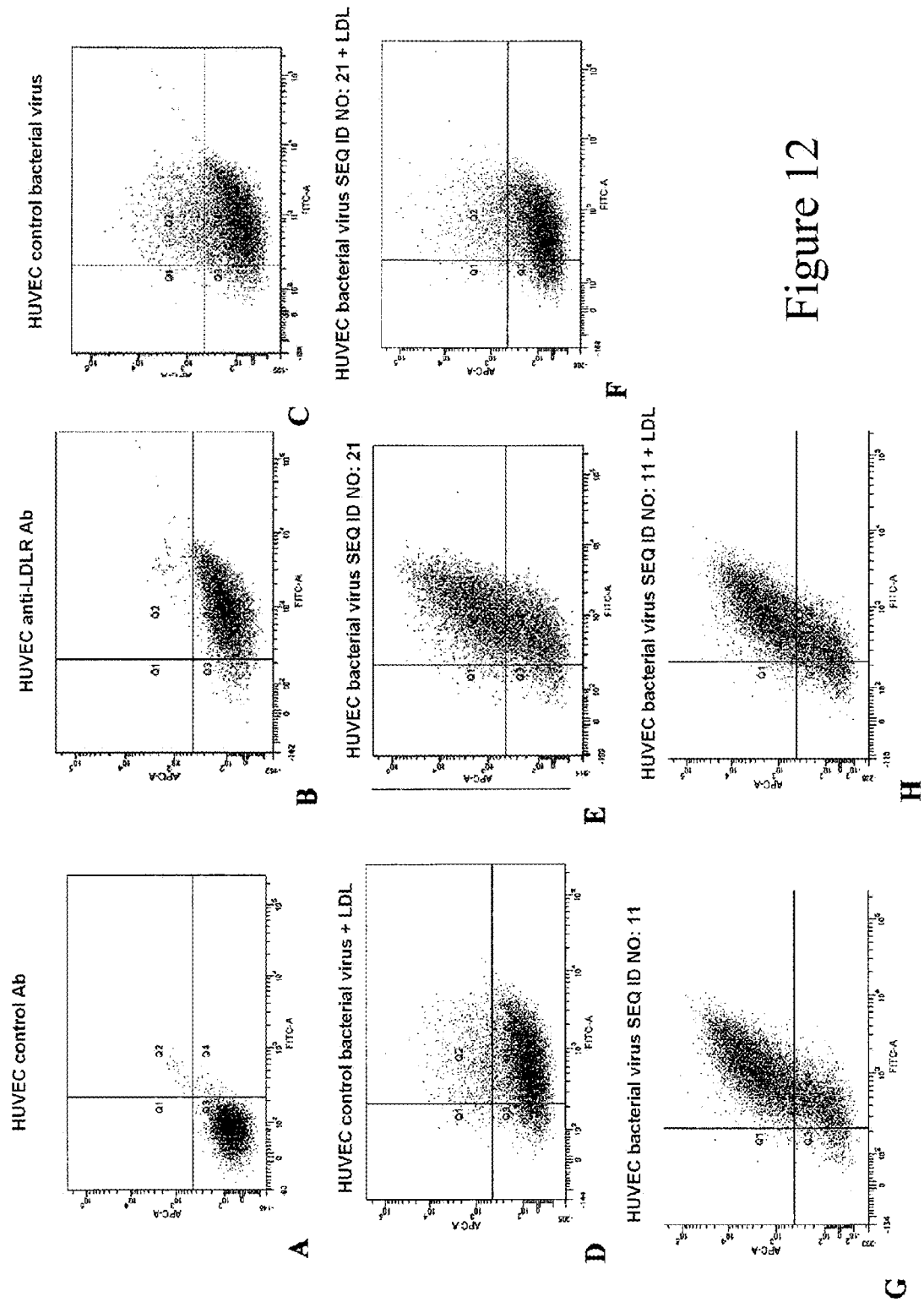
Figure 12:
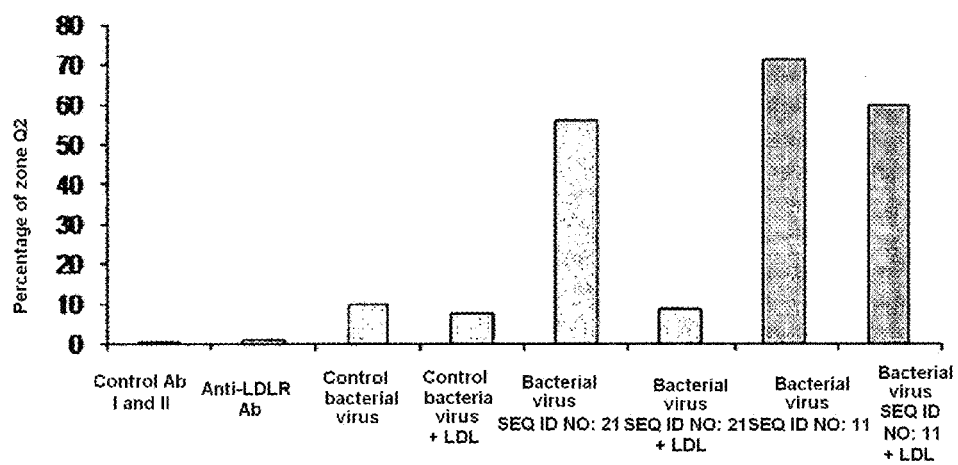
Figure 13:
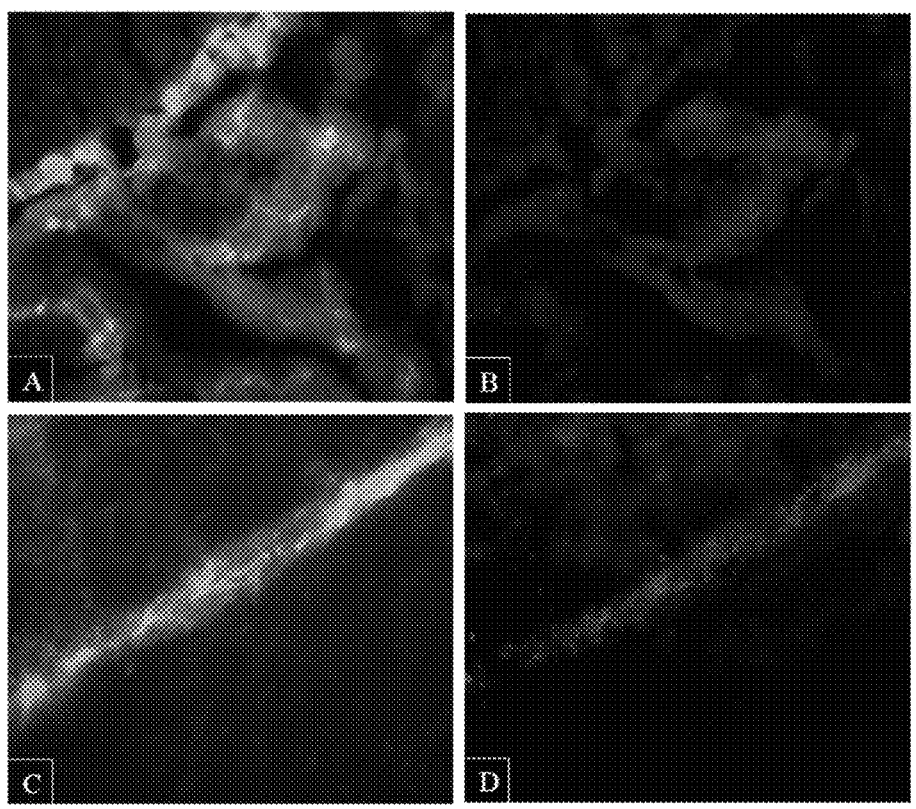

The hypothesis, according to which peptides expressed by bacterial viruses with affinity for hLDLR could interact with LDL binding domains, the natural ligand of hLDLR, was evaluated on various cell types, notably on HUVEC by FACS experiments, similar to those presented above, as shown here for example (FIG. 12). First, it is shown that the binding rate of bacterial viruses expressing peptides with affinity for hLDLR (SEQ ID NO: 21 and SEQ ID NO: 11 are used here as examples) is proportional to the level of LDLR expression by HUVEC. FACS experiments carried out in the presence of LDL made it possible to show and quantify a strong shift (85%) of LDL by linear peptides (for example SEQ ID NO: 21), but a small shift (17%) by cyclic peptides (for example SEQ ID NO: 11).

Example V

Interaction of peptides expressed by bacterial viruses with affinity for hLDLR with mouse brain vessel endothelial cells in vivo.

Bacterial viruses expressing peptides with affinity for hLDLR (SEQ ID NO: 1 is described here for example) and control bacterial viruses (not expressing peptide with affinity for hLDLR) were injected into the tail veins of C57BL6 mice anaesthetised with halothane. After 15 min and 2 h post injection, the mice were sacrificed and perfused with 0.9% NaCl. Brains, livers and kidneys were frozen in isopentane and frozen sections were prepared for double immunohistochemical staining to visualise blood vessels with anti-mouse IgG and anti-viral envelope protein antibody to visualise bacterial viruses bound to endothelial cells in vivo. The experiments show that bacterial viruses expressing peptide SEQ ID NO: 1 with affinity for hLDLR and mLDLR bind to vessel wall endothelial cells, which is not the case for control bacterial viruses (FIG. 13).

Example VI

Synthesis of peptides corresponding to bacterial viruses with affinity for hLDLR and coupling with a tracer molecule (biotin, fluorescein, or S-Tag with enzymatic activity).

Peptides were synthesised by the solid phase peptide synthesis (SPPS) method on an Advanced ChemTech Apex396 (AAPPTec) synthesiser, or a Liberty™ (CEM) microwave synthesiser, using an Fmoc/tBu strategy on Rink Amide AM resins on polystyrene-1% DVB, Wang on polystyrene-1% DVB, Barlos (2-chlorotrityl chloride) on polystyrene-1% DVB, or Sieber Amide on polystyrene-1% DVB. The load (or substitution) is between 0.25 mmol/g and 1.6 mmol/g according to the resin used.

The amino acids N-protected by Fmoc (or Boc for some N-term ends) and/or protected by orthogonal functions (notably acid labile functions) at their side chains, the chemical coupling and deprotection reagents and the solvents are bought from specialised companies and are used as-is.

The Rink Amide and Wang resins make it possible to synthesise peptide sequences completely deprotected on their side chains and their C-term ends. This is thus 2-dimensional (Fmoc/tBu) orthogonal SPPS.

Barbs and Sieber hypersensitive acid labile (HAL) resins enable the release of the terminal (C-term) acid or amide function while preserving the orthogonal side protections of the various amino acids of the synthesised peptide as well as the terminal (N-term) amine protection of the amine function of its last amino acid (for example, N-acetylation for questions of stability of the neosynthesised peptide sequence). These types of resins, via an Fmoc ($Prot_1$) synthesis strategy, make it possible to use acid-labile orthogonal side protections ($Prot_2$: Boc, tBu, OtBu, Trt, Mmt, Acm, etc.) cleavable only in a strongly acid medium, whereas the protected peptide is uncoupled in very weak acid conditions. This type of cleavage makes it possible to recover the peptide sequence completely protected on its side functions ($Prot_2$) with a view to coupling the therapeutic molecule of interest with the peptide. This is thus three-dimensional (Barlos or Sieber/Fmoc/tBu) orthogonal SPPS.

The standard orthogonal side protections ($Prot_2$) used for each amino acid during peptide synthesis are: Arg(N-Pbf), Arg(N-Pmc), Asn(N-Trt), Asp(O-tBu), Cys(S-Acm), Cys(S-Mmt), Cys(S-4MeBn), Cys(S-tBu), Cys(S-Tmob), Cys(S-Trt), Glu(O-tBu), Gln(N-Trt), His(N-Trt), Lys(N-Boc), Ser (O-tBu), Thr(O-tBu), Trp(N-Boc), Tyr(O-tBu) (*Applied Biosystems,* 1998, *Cleavage, Deprotection, and Isolation of Peptides after Fmoc Synthesis. Technical Bulletin*). Gly, Ala, Val, Leu, Ile, Phe, Met and Pro do not have side protections, since their respective chemical structures do not require it.

Amino acids are coupled via activation of the acid function of the n+1 amino acid using DIEA/HBTU/HOBt or DIPC/HOBt in DMF.

Deprotection of the Fmoc ($Prot_1$) group of a new amino acid thus coupled is carried out using 20% piperidine in DMF.

The last amino acid coupled during peptide sequencing will either be protected by a Boc function (with a view to releasing its free terminal amine function at the end of synthesis), or acetylated (in order to stabilize the synthesised neopeptide but also to reduce the risks of secondary reactions during covalent coupling of the therapeutic molecule of interest in the C-term position, for example).

According to the peptide synthesised, disulphide bridges are obtained by intramolecular cyclisation from two thiol functions of two suitably protected Cys (Acm, Trt, tBu, etc.), either in solution or on resin, using reagents classically used by the person skilled in the art: $I_2$/DMF, $I_2$/HFIP/DCM, TFA/DMSO/anisole, $I_2$/DCM/MeOH/$H_2O$, etc. A Cys in the N-term position can advantageously be replaced by an Mpa for cyclisation via a disulphide bridge. Lanthionine bridges (by cyclisation via dehydroalanine) or dicarba (by cyclisation via allylGly) can also be obtained by synthesis pathways known to the person skilled in the art. A lactam bridge can be created between the side acid function of a Glu (or Asp) residue and a side amine function on a Lys or an N-term amine. Similarly, cyclisation between the N-term amine function and the C-term acid function (head/tail) can be carried out via an amide bond, just as cyclisation between the side amine function of Lys and the C-term acid function of the peptide.

Peptides from Barlos or Sieber resins are cleaved by methods classically used by the person skilled in the art, either with 0.5% TFA (v/v) in DCM, or with AcOH/TFE/DCM (1/1/3), or with HFIP (30%) in DCM, or with TFE (30%) in DCM, etc.

Deprotection of side chains, and cleavage of peptides from Rink Amide or Wang resins, are carried out by methods classically used by the person skilled in the art: either with TFA/$H_2O$/TIS or TIPS (95/2.5/2.5), or with TFA/$H_2O$/EDT/TIS or TIPS (94/2.5/2.5/1), or with TFA/thioanisole/$H_2O$ (94/5/1), or with TFA/TIS/$H_2O$/thioanisole (90/5/3/2), or with TFA/$H_2O$/phenol/thioanisole/EDT (82.5/5/5/5/2.5), etc.

Biotins, fluoresceins, or S-Tag (see EXAMPLE VII, below) are introduced in the C-term position according to classic synthesis and coupling methods known to the person skilled in the art.

Peptides are isolated and purified by HPLC on Beckman System Gold 126 equipment with a Chromolith C18 (4.6 mm×50 mm) or Nucleosil C18 (10 mm×250 mm) column with, for example, a 0% to 100% acetonitrile gradient in an aqueous phase ($H_2O$+0.1% TFA) in 3.5 min, then 100% to 0% in 1.5 min (flow rate: 1 ml/min to 5 ml/min), or on a Waters 1525 system with a Chromolith Speed ROD RP-18 (4.6 mm×50 mm) column (stationary phase) with detection by a Waters 996 PDA detector (190 nm-400 nm), or on a Waters Alliance 2690 system with a Chromolith Performance RP-18 (3 mm×100 mm) column (stationary phase) with detection by a Waters 996 PDA detector (190 nm-400 nm). UV detection is carried out at 214 nm and 254 nm.

Preparative purifications are carried out with a Waters Prep LC 4000 system with a Guard-Pak™ column (stationary phase) with Delta-Pak™ C18 cartridges (25 mm×10 mm) with detection by a Waters 2487 Dual Wavelength Absorbance Detector.

Molecular weights are determined using an electrospray ionisation (ESI) mass spectrometer in positive mode. The spectra are obtained by using a Waters Micromass Quattro Micro (quadrupole analyser) equipped with a Waters Alliance 2690 HPLC system enabling LC-MS coupling.

The LC-MS analysis conditions used are as follows:
Chromolith Flash C18 column (4.6 mm×25 mm),
3 ml/min flow rate,
linear gradient from 0% to 100% of B in 2.5 min (A: 0.1% $H_2O/HCO_2H$; B: 0.1% $ACN/HCO_2H$).

Mass spectra in positive electrospray mode are acquired at a flow rate of 100-200 μl/min. The data are obtained in scan mode from 200-1700 m/z with 0.1 s intervals.

Example VII

Binding and endocytosis of synthesised peptides with affinity for hLDLR in CHO-LDLR-GFP cell lines.

Figure 14:
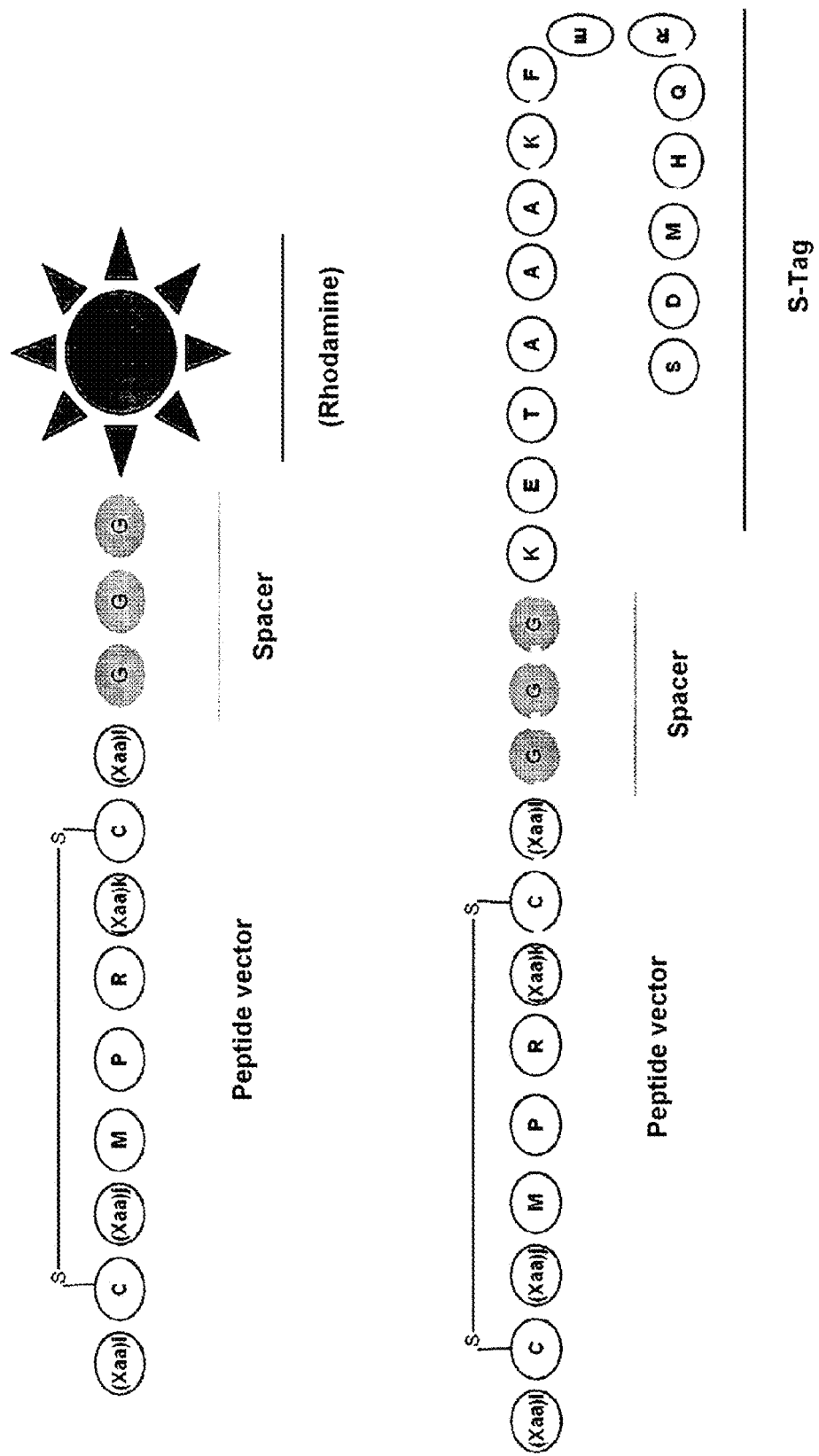

Peptides with affinity for hLDLR-GFP and control peptides (random peptides, residues identical to the peptides with affinity for hLDLR-GFP but in no particular order) were synthesised, and coupled/conjugated in the C-term position with various tracer molecules, either rhodamine or S-Tag, separated by a spacer composed of three Gly residues (FIG. 14). S-Tag (a 15 amino acid peptide derived from sequence 1-15 of bovine pancreatic ribonuclease A) on the one hand can be recognised by an anti-S-Tag antibody for immunocytochemistry or FACS approaches, and on the other hand can reconstitute enzymatic activity by binding with ribonuclease S-protein (C-term portion, amino acids 21-124) in tests of activity in vitro using the FRETWorks S-Tag assay kit (Novagen 70724-3). The ribonuclease thus activated digests an RNA substrate releasing a masked fluorescent agent visualised by FRET (fluorescence resonance energy transfer) and quantified in a 96-well plate in a Beckmann spectrofluorimeter. For these FRET experiments, control CHO cells and GFP fused in the C-term position with hLDLR and mLDLR, which generates strong background noise at the wavelengths used for FRET, was replaced by red fluorescent protein (RFP). The stable cell lines generated for the FRET experiments are thus CHO-RFP and CHO-hLDLR-RFP.

For the FRET approaches, cells are washed twice with 2 ml PBS and then incubated for 1 h at 37° C. with 250 μl peptide solution. They are again washed twice with 2 ml PBS and then twice with 1 ml PBS, and then scraped in 1 ml PBS and centrifuged for 5 min at 1,250 rpm. The supernatant is then aspirated and the cell pellet is lysed in 80 μl PBS+0.1% Triton X100. Twenty μl of each cell lysate are analysed by measuring fluorescence emission after the FRET reaction.

Figure 15:
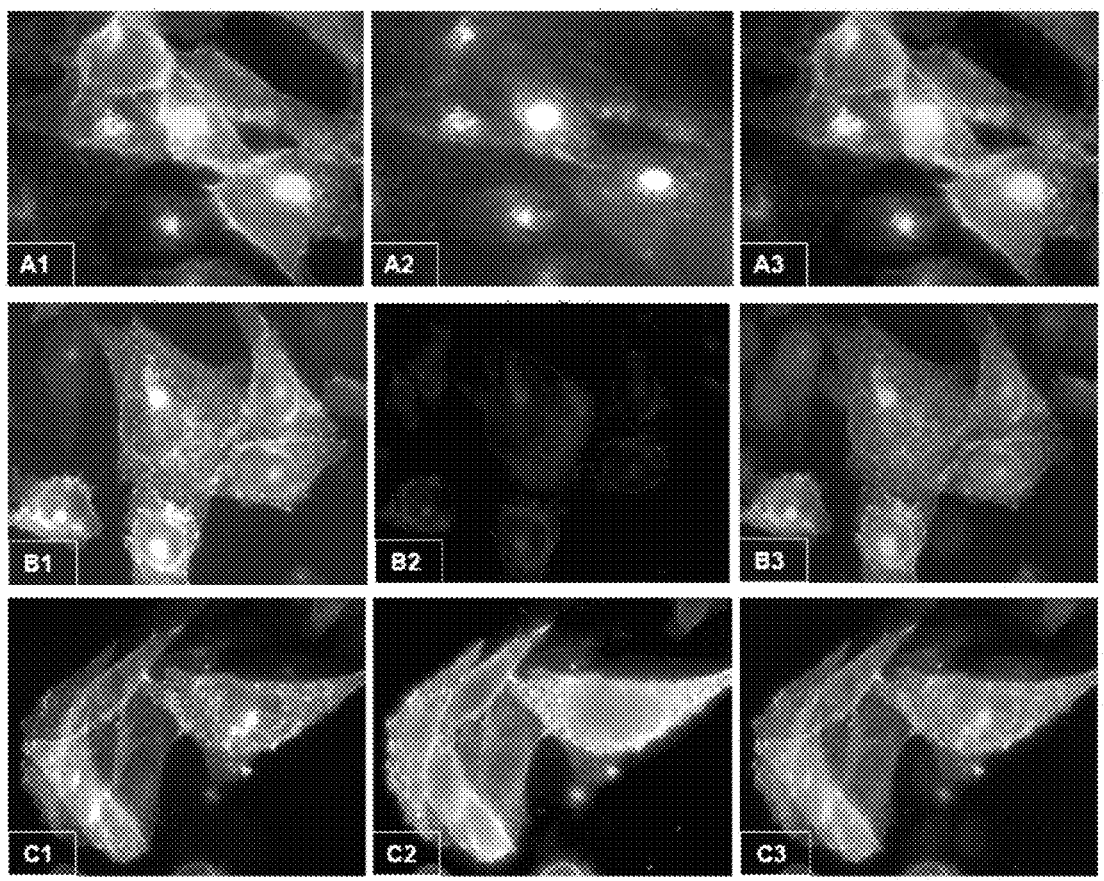

Experiments involving the incubation of peptides on various cells expressing hLDLR were performed. The results obtained with peptide SEQ ID NO: 1 conjugated with rhodamine or peptide SEQ ID NO: 2 conjugated with S-Tag are shown as an example and indicate that the peptides bind well to CHO-LDLR-GFP cells and that they are incorporated by endocytosis to accumulate in the cells of the cell line that expresses hLDLR, which is not the case for the control peptides (FIG. 15). In these experiments, preliminary incubation of peptides conjugated with S-Tag, with a primary antibody (primary Ab) directed against S-Tag, and a secondary antibody (secondary Ab) directed against the primary antibody show that the SEQ ID NO: 2/S-Tag/primary Ab/secondary Ab complex binds to cells expressing hLDLR and is internalised by endocytosis. These results indicate that peptides of the SEQ ID NO: 2 family can bind to cells expressing hLDL and vectorise large loads (two antibodies), i.e., these loads are internalised by endocytosis.

Figure 16:
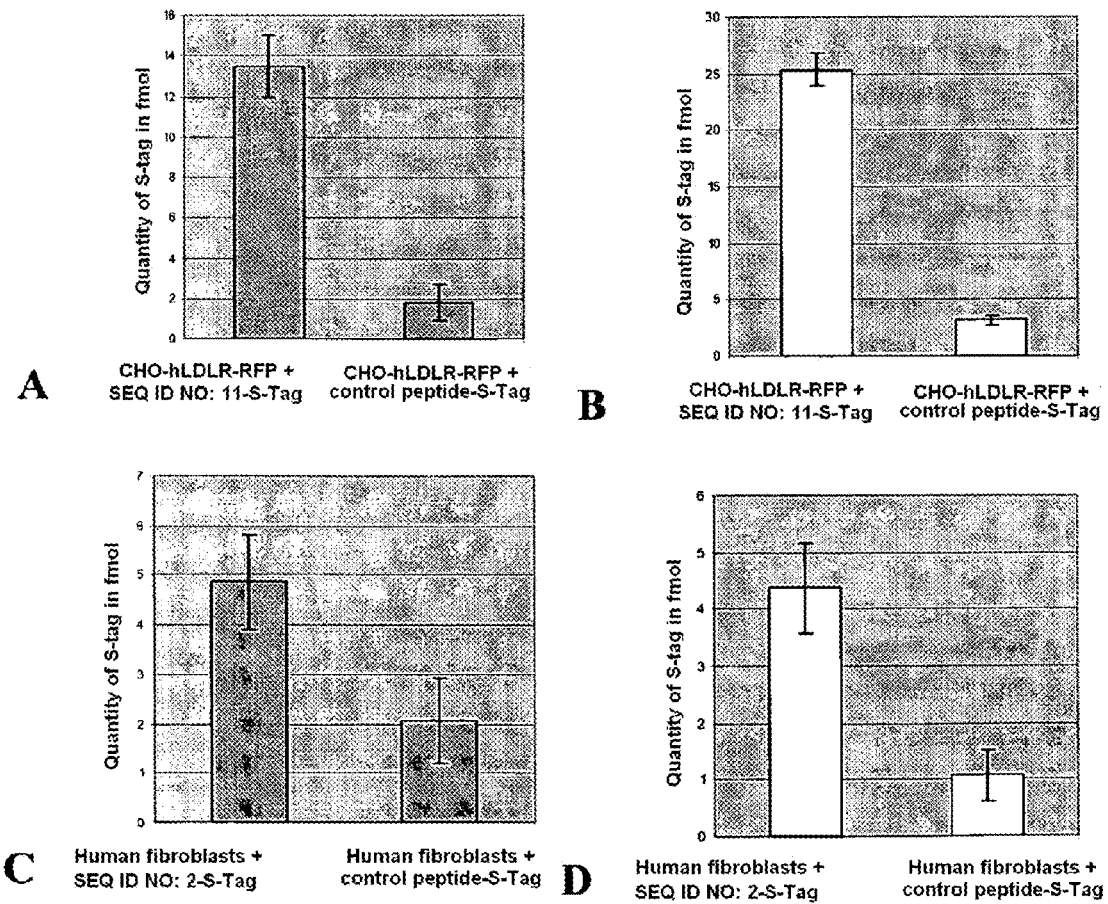

Endocytosis of peptides with affinity for hLDLR was quantified. To this end, SEQ ID NO: 11/S-Tag and control (random) peptides were incubated with CHO-hLDLR-RFP cells for 1 h at 37° C. The cells were washed in order to eliminate any trace of non-fixed peptide. The washings were carried out with PBS, which makes it possible to quantify by FRET the peptides bound to the cell membrane and those internalised by endocytosis (FIG. 16-A), as well as with an acid solution (0.2 M glycine, 0.15 M NaCl, pH 3), which makes it possible to dissociate the peptides bound to hLDLR at the cell membrane. Only peptides incorporated by endocytosis by the cells are then detected by FRET (FIG. 16-B). The same is true with peptide SEQ ID NO: 2/S-Tag on human fibroblasts (FIG. 16-C-D).

Figure 17:
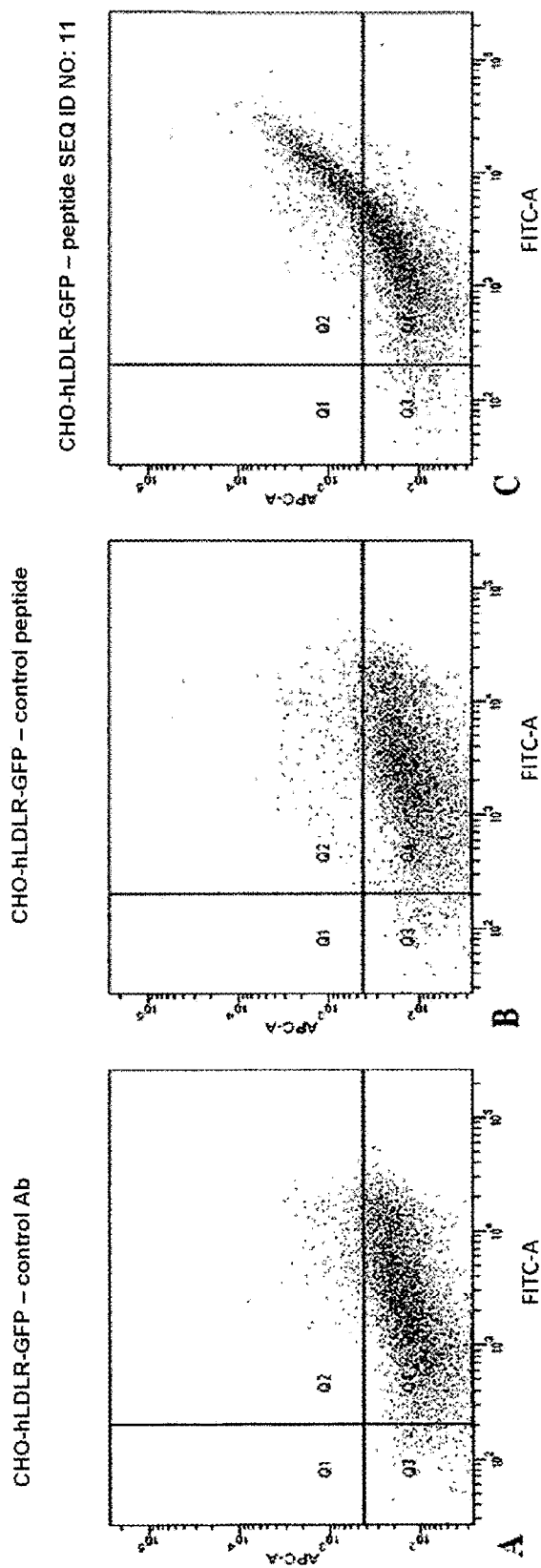

These observations were also confirmed on non-adherent cells by FACS. An example is given of binding on cells of the CHO-hLDLR-GFP cell line of peptide SEQ ID NO: 11 conversely to the control peptide, both being conjugated with S-Tag (FIG. 17).

Example VIII

Toxicity, endocytosis and transcytosis of synthesised peptides with affinity for hLDLR on endothelial cells in an in vitro BBB model.

The potential toxic effects of peptides on endothelial cells, the binding/accumulation of peptides in these cells, and the passage by transcytosis of peptides were evaluated on in vitro BBB models. The cells necessary to set up the model (co-culture of endothelial cells from brain microvessels and astrocytes) are bovine cells (bovine brain microvascular endothelial cells, BBMEC) sold by Cellial Technologies (Lens, France). This in vitro BBB model is used to evaluate the passive passage/diffusion or active transport of numerous molecules, notably pharmacological agents, across the BBB and thus their capacity to reach CNS tissue. The model has ultrastructural properties characteristic of the brain endothelium, notably tight junctions, absence of pores, absence of transendothelial channels, low permeability to hydrophilic molecules and high electrical resistance. Moreover, this model showed a solid correlation between the results of measurements taken on various molecules evaluated in vitro and in vivo for their property of passing across the BBB. To date, all the data obtained show that this BBB model closely imitates the situation in vivo by reproducing some of the complexities of the cell environment that exist in vivo, while preserving the advantages associated with tissue culture experimentation. Numerous studies have validated this cell co-culture as one of the most reproducible in vitro BBB models.

The in vitro BBB model brings into play a co-culture of BBMECs and astrocytes. Prior to cell culture, membrane inserts (Millicell-PC 3.0 μm; 30 mm diameter) are treated on the upper part with rat tail collagen in order to enable optimal adhesion of BBMECs and to create the conditions of a basal lamina. Primary cultures of mixed astrocytes are established from neonatal rat cerebral cortex (Dehouck et al., 1990, *J. Neurochem.*, 54, 1798-1801). Briefly, after the meninges are removed, the brain tissue is passed through an 82 μm nylon sieve. The astrocytes are distributed in microplate wells at a concentration of $1.2 \times 10^5$ cells/ml with 2 ml optimal culture medium (DMEM) supplemented with 10% heat-inactivated foetal calf serum. The medium is changed twice per week. The BBMECs obtained from Cellial Technologies are grown in the presence of DMEM medium supplemented with 10% (v/v) horse serum and 10% heat-inactivated calf serum, 2 mM glutamine, 50 μg/ml gentamicin and 1 ng/ml basic fibroblast growth factor, added every two days. The BBMECs are then distributed on the upper surface of the filters in 2 ml co-culture. This BBMEC medium is changed three times per week. Under these conditions, differentiated BBMECs form a monolayer of confluent cells seven days later. The experiments reported below are carried out between five and seven days after confluence was reached.

Peptide SEQ ID NO: 1 and a control peptide, both conjugated with rhodamine, were incubated in the upper chamber of the culture system, in contact with endothelial cells for 1 h, 5 h and 24 h. The culture medium of the lower chamber is collected at various times and fluorescence quantified by fluorimetric analysis. The results are expressed as endothelial surface permeability (Pe) in units of $10^{-3}$ cm/min. Lucifer Yellow (LY), a small fluorescent molecule which crosses the BBB very little, is used first to evaluate the integrity of the BBB in vitro, in all the wells analysed, and second for peptide co-incubation in order to evaluate the absence of toxicity of the peptides for the endothelial cells that form this BBB. The in vitro barrier is considered "permeable" or "open" if the Pe value of LY is greater than $1 \times 10^{-3}$ cm/min. Transendothelial electrical resistance (TEER), measured with an ohmmeter and expressed in ohm·cm$^2$, also makes it possible to measure BBB integrity in vitro during tests of passage across the BBB. The quality threshold value is set at >500 ohm·cm$^2$.

Figure 18:
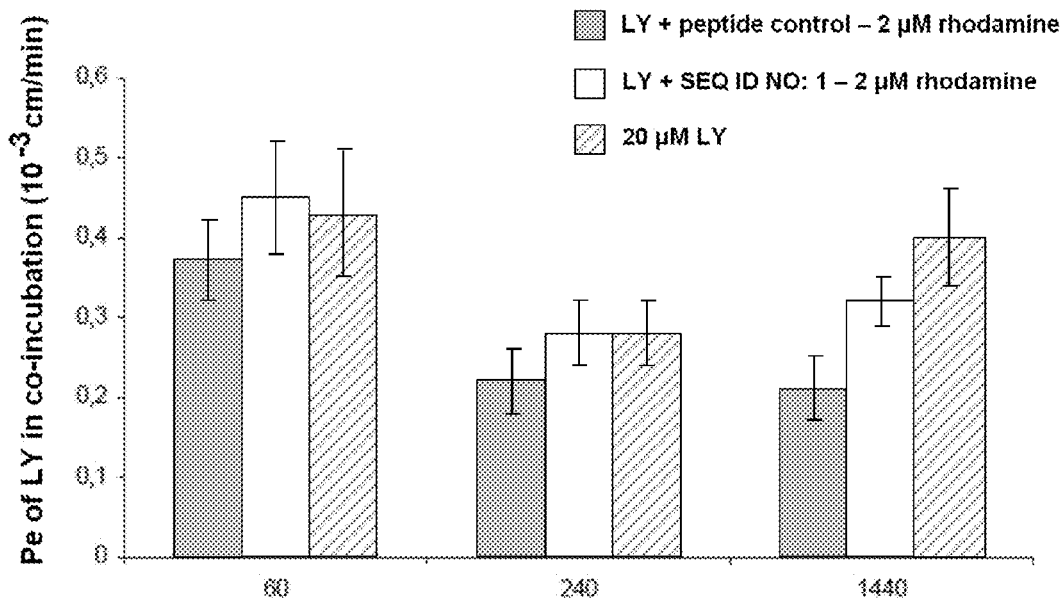

Analyses carried out with the peptides show an absence of toxicity for peptide SEQ ID NO: 1, as well as for the control peptide used, and an absence of deleterious effects on the permeability properties of the BBB, since the Pe values measured with LY do not increase in the presence or absence of the peptides, even after 24 h of incubation (FIG. 18).

Figure 19:
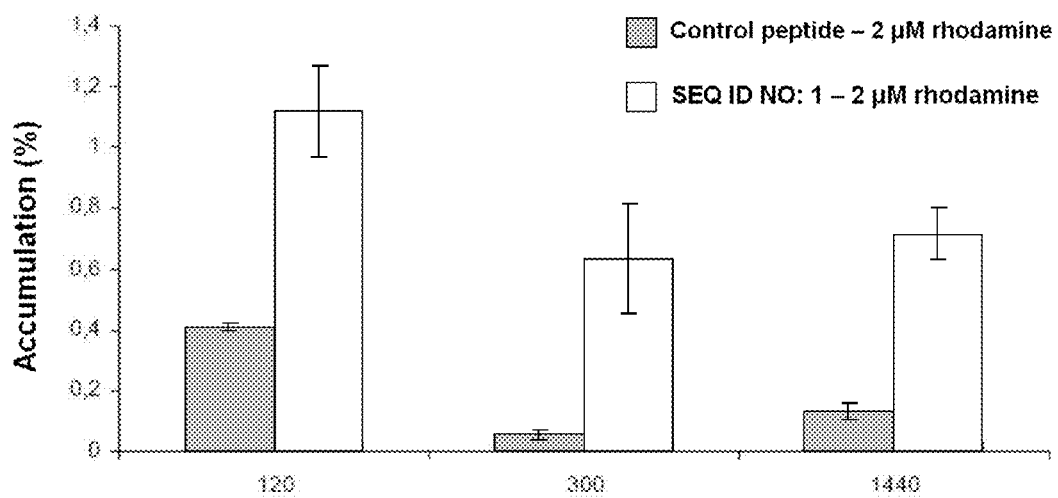

The binding and/or internalisation rate of a control peptide and peptide SEQ ID NO: 1, both conjugated with rhodamine, was determined on the in vitro BBB model described above. This analysis was carried out by lysis of endothelial cells at various times (2 h, 5 h, 24 h), and by fluorimetric measurements of the quantity of fluorescence (rhodamine) associated with the cells (membrane and cytoplasmic compartments obtained by centrifugation of these cells after lysis). The measured values indicate that peptide SEQ ID NO: 1 conjugated with rhodamine has more affinity for endothelial cells in an in vitro BBB model than the control peptide, at all times analysed (FIG. 19).

Figure 20:
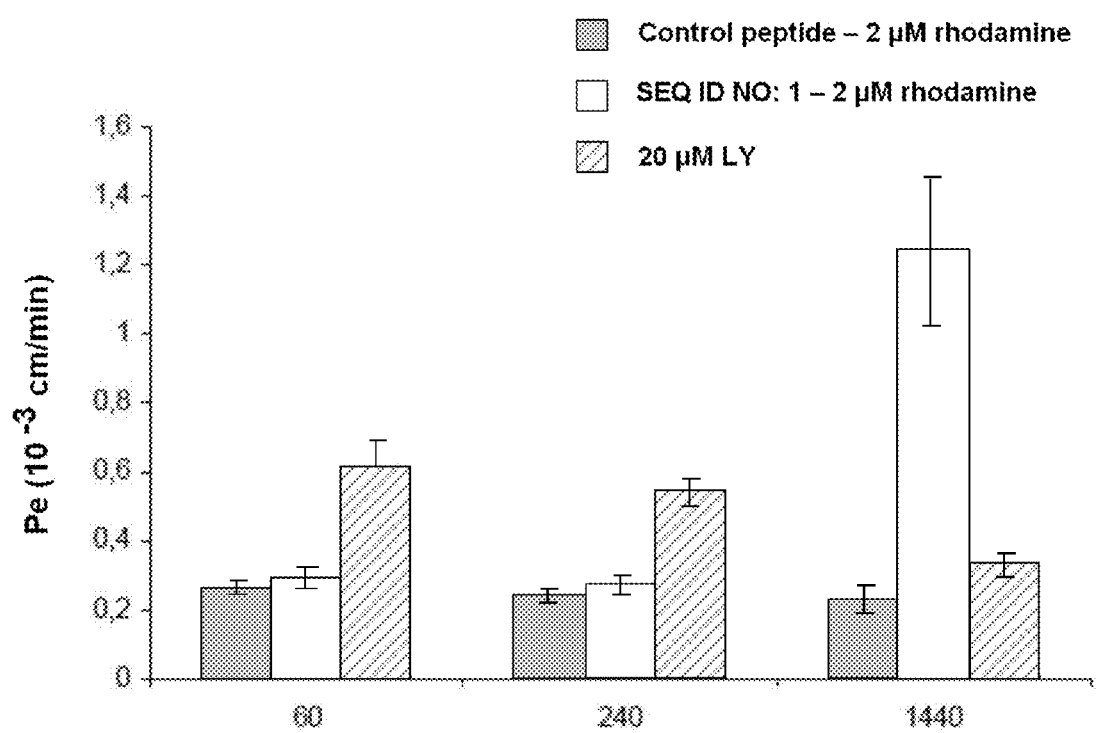

The passage of a control peptide and peptide SEQ ID NO: 1, both conjugated with rhodamine, was established on the in vitro BBB model described above. This analysis is carried out by measuring by fluorimetry the quantity of fluorescence accumulated in the receiver wells at various times (1 h, 4 h, 24 h). The integrity of the BBB in the various wells analysed was evaluated by simultaneous measurement of the level of LY that passes from one compartment to the other as a function of time. The Pe values measured indicate that in short periods (1 h and 4 h), the level of peptide SEQ ID NO: 1 that passes by transcytosis cannot be distinguished from nonspecific or paracellular passage as measured for the control peptide. On the other hand, at 24 h, the rate of passage of peptide SEQ ID NO: 1 conjugated with rhodamine is quite significantly higher than that of the control peptide. Measurements of LY also show that the integrity of the BBB is preserved at 1 h, 4 h and 24 h (FIG. 20). Other measurements show that the concentration of peptide SEQ ID NO: 1 conjugated with rhodamine is much higher in the receiver compartment at 24 h, compared with that of the donor compartment, suggesting active transport of the peptide, certainly via receptors, without an equilibrium of concentration having been reached between the two compartments.

Example IX

Chemical Optimisation of Peptide Vector SEQ ID NO: 11

A study of the structure/activity (affinity) relationships was carried out on peptide vector SEQ ID NO: 11 via the alanine scanning (Ala-scan) technique and by N- and C-term truncation in order to determine the importance of each of the 15 constitutive amino acids of this peptide. Affinity for hLDLR of each neosynthesised peptide resulting from chemical optimisation was determined by fluorimetry by measuring the displacement rate of peptide SEQ ID NO: 11 conjugated at the C-term via a three-Gly spacer to S-Tag peptide (SEQ ID NO: 11/S-Tag) (see EXAMPLE VII). Briefly, the CHO-hLDLR-RFP cells used are adherent and at confluence.

They are grown in six-well plates. Three wells of cells are used per condition.

A solution containing 10 μM peptide SEQ ID NO: 11/S-Tag is prepared in HamF12-1% BSA culture medium. To this solution is added 10 μM peptide resulting from the Ala-scan to be evaluated (competition).

Several control solutions are also prepared:
(i) HamF12-1% BSA medium,
(ii) HamF12-1% BSA medium+10 μm control peptide CTRL-S-Tag (evaluation of nonspecific binding of any peptide comprising S-Tag).
(iii) HamF12-1% BSA medium+10 μm peptide SEQ ID NO: 11/S-Tag+10 μm control peptide CTRL (evaluation of "nonspecific" competition between the peptide of interest and the control peptide CTRL).

The FRET approaches used are those described in EXAMPLE VII.

Roughly 60 peptides were tested by these approaches. Thirty-six of these peptides (SEQ ID NO: 30 to SEQ ID NO: 65) exhibit in vitro affinity for LDLR.

This study further confirmed the importance of cysteines and thus of the cyclisation and of the MPR tripeptide motif.

This study also made it possible to reduce the size of the peptide vector since the cyclic peptide of eight amino acids (SEQ ID NO: 48), comprising at least one amino acid of D-configuration, exhibits excellent affinity for LDLR.

According to the same protocol, SEQ ID NO: 48/S-Tag serves as a reference for chemical optimisation (study of cycle size, introduction of non-natural amino acids) of peptide vector SEQ ID NO: 48 and measurements of the affinity of conjugates for LDLR.

Thus, the conjugates SEQ ID NO: 66 to SEQ ID NO: 72, described in the present application, also exhibit in vitro affinity for LDLR.

Example X

Strategy for chemical synthesis of conjugates comprised of a vector and a therapeutic molecule of interest or imaging (or diagnostic) agent or any other molecule such as a molecular probe.

A therapeutic molecule of interest or imaging or diagnostic agent or any other molecule such as a molecular probe can be released/cleaved from the vector after transport and passage across cell membranes, more particularly the BBB, for example through a prodrug strategy by hydrolysis or enzymatic cleavage of a chemical bond between the vector and the active substance.

Covalent coupling between the peptide vector completely protected on its reactive side functions (coupling at the C-term and N-term) or partially protected (coupling on a reactive function of a side chain) and the therapeutic molecule of interest is carried out via two general strategies (FIG. 2):
synthesis in tandem (i.e., direct coupling with no intermediate between the two entities), or
synthesis via a linker (Temsamani et al., 2004, *Drug Discov. Today*, 23, 1012-1019).

As an example, synthesis in tandem of peptide conjugate SEQ ID NO: 66 between an analgesic therapeutic peptide, dalargin, and peptide vector SEQ ID NO: 48 was carried out as described for the synthesis of peptides in EXAMPLE VI.

As an example, syntheses via peptide linkers (GGG, GFLG, ALAL, β-Ala, Ahx, GFAL) of peptide conjugates SEQ ID NO: 67 to SEQ ID NO: 72 between an analgesic therapeutic peptide, dalargin, and peptide vector SEQ ID NO: 48 were carried out as described for the synthesis of peptides in EXAMPLE VI.

According to the peptide vector and molecule of therapeutic interest selected, one or the other of the various strategies is applied either on the C-term, or on the N-term, or on a side chain reactive function. Ideally, the spacers selected should enable suitable release of the active substance and improvement of the solubility of the conjugate (Molema et al., 2001, *Vectorisation, organ-specific strategies*. In: *Methods and principles in medicinal chemistry*, vol. 12). Various labile covalent chemical bonds can thus be generated between the two entities (vector and active substance) via or not via a spacer: amides, carbamates, esters, thioester, disulphide, etc. For example, it has been shown in the literature that disulphide bonds, relatively stable in plasma, can be cleaved inside the intracerebral compartment to restore a free thiol function (Saito et al., 2003, *Adv. Drug Deliv. Rev.*, 55, 199-215).

Other compounds of interest are those wherein the spacer is a polymer such as polyethylene glycol (PEG). Indeed, it has been shown in the literature that the conjugation of an organic molecule of biological interest with PEG made it possible to increase the plasma half-life of this molecule (Greenwald et al., 2003, *Adv. Drug Deliv. Rev.*, 55, 217-250) and to decrease its clearance.

Conjugates between vectors and an active substance or a substance of interest can be used in the diagnosis, imaging or therapy of a pathology, lesion or disorder of the CNS for preparing a drug capable of crossing the BBB, a brain tumour or another type of cancer cell, for preparing a drug capable of crossing cancer cell membranes, and/or infectious pathologies for preparing a drug capable of crossing cell membranes and to target the infected cells of bacterial, viral, parasitic or fungal infectious pathologies of the brain or other tissues/organs.

Example XI

In situ brain perfusion for vectors alone and conjugates between vectors and a therapeutic molecule of interest or an imaging (or diagnostic) agent or any other molecule such as a molecular probe, and study of their transport kinetics across the BBB and their accumulation in the mouse brain.

The in situ brain perfusion technique (in adult male OF1 mouse) is used here to select the best vectors and to provide proof of their mechanism of action for their passage in the brain across the BBB.

Beforehand, the peptide vectors are radiolabelled with tritium ($^3$H), which offers the strongest sensitivity for the detection of radioactive compounds, notably on tissue sections. Radioactive peptides with high specific radioactivity (SRA, up to 100 Ci/mmol) are prepared by a strategy of acylation of the N-term amine function by tritiated propionic (or propanoic) anhydride or tritiated N-propionyl-succinimide (NPS). This tritiation method can be applied to all peptides, provided that modification of the N-term does not affect the affinity of the peptides for the targeted receptor (i.e., LDLR) or their biological activity in the case of therapeutic peptides.

The tritiation reaction of peptide vectors SEQ ID NO: 11 and SEQ ID NO: 48 in the N-term position by propionylation is carried out in DMF (1 mg peptide in 100 μl to 450 μl according to solubility) by adding 0.1 equivalent of tritiated NPS for 5 min at room temperature, then 0.9 equivalent of cold NPS (non-tritiated) for 1 h, and then a new equivalent of cold NPS for 5 h. The reaction medium is then left at 4° C. overnight and purified the following day by HPLC. The SRA for each tritiated peptide is between 5 Ci/mmol and 10 Ci/mmol (theoretically on the order of 7.7 Ci/mmol). The total quantity of radioactivity prepared by synthesis is between 600 μCi and 950 μCi.

In the case of conjugates between vectors and an active substance, it is important, to avoid radiolabelled chemical syntheses requiring the development of long and costly new synthesis pathways, to choose a model active substance already commercially available with carbon-14 ($^{14}$C) labelling. Radiolabelled peptides (radiolabelled with $^3$H, for example) are coupled covalently with a radiolabelled active substance (radiolabelled with $^{14}$C, for example) as described in EXAMPLE X. As previously mentioned, this covalent coupling is carried out according to the structure and physicochemical properties of the active substance, in particular the presence of functional chemical groups that can be modified without decreasing the biological activity of this substance. Radiolabelled conjugates are synthesised by extrapolation from synthetic pathways developed for non-radiolabelled conjugates.

Another strategy consists of the synthesis of a conjugate between a therapeutic peptide and a peptide vector via a linker (of peptide or organic nature) or not via a linker, as in the case of conjugates SEQ ID NO: 66 to SEQ ID NO: 72 described in the present application. Thus, the N-term tritiated conjugate SEQ ID NO: 72 was prepared as described above.

The techniques briefly summarised below were developed to study the distribution in the brain of active substances and, in particular, the role of the BBB and, more particularly, of LDLR in the penetration of these molecules in the brain. In situ brain perfusion techniques are among the most technically demanding and the most difficult to perform in the mouse. However, in situ brain perfusion (like in vitro models) enables total control of the composition of the artificial perfusate in order to maintain the cells and vascularisation of the brain under normal physiological and anatomical conditions within the animal, without the disrupting factor of systemic distribution.

This strategy of in situ brain perfusion normally carried out in the rat was adapted for mouse (Dagenais et al., 2000, *J Cereb Blood Flow Metab.*, 20(2), 381-6) in order to broaden its application for evaluating the parameters of transport kinetics at the BBB and the blood-retinal barrier, in transgenic and KO mutant mice for the receptors, enzymes or transporters of active substances. It involves catheterisation of a carotid artery in anaesthetised OF 1 mice and ligature of some branches of this carotid artery (external, thyroidal, occipital) in order to specifically perfuse the internal carotid and pterygopalatine arteries, which are used to evaluate the uptake in the brain of the vectors and conjugates. The catheter makes it possible to replace general circulation by infusion with a well-controlled perfusate (bicarbonate buffer, plasma or blood) by passing by the carotid. Oxygenated Krebs bicarbonate buffer is first used to evaluate the capacities of the vectors and conjugates to gain access to the brain. After catheterisation of the carotid, endogenous blood flow is stopped by sectioning the ventricles of the heart in order to avoid the mixture of buffer with blood and elevation in blood pressure. The duration of the fixed flow-rate perfusion is monitored. The buffer perfusion can be extended up to 20 min, or up to 1 h in the presence of oxygen transporters (washed erythrocytes) for studies of receptor-mediated transport (RMT).

The study of peptide vector SEQ ID NO: 11 made it possible to determine its brain transport or transfer coefficient ($K_{in}$). The duration of brain perfusion for these experiments is 5 min with a perfusate flow rate of 2 ml/min. Thus, the calculation of the $K_{in}$ (volume of distribution over time of brain perfusion) of peptide vector SEQ ID NO: 11 gives a value of $3.5 \pm 0.2 \times 10^{-4}$ ml/s/g.

It should be noted that transferrin (TO has a $K_{in}$ of $3.0 \times 10^{-4}$ ml/s/g (Demeule et al., 2008, *J. Neurochem.*, 106(4), 1534-1544). The $K_{in}$ of RAP protein is $1.0 \times 10^{-5}$ ml/s/g (Pan et al., 2004, *J. Cell Sci.*, 117, 5071-5078).

The chemical optimisation of peptide vector SEQ ID NO: 11 in an optimised peptide vector SEQ ID NO: 48 enabled an improvement of passage in the brain of the peptide vector by a factor of 1.37. Peptide SEQ ID NO: 73, CMPRC was used as a control for this brain perfusion study.

$K_{in}$ of SEQ ID NO: 48=$4.8 \pm 0.4 \times 10^{-4}$ ml/s/g $K_{in}$ of SEQ ID NO: 73=$1.5 \pm 0.2 \times 10^{-4}$ ml/s/g As previously described, the chemical conjugation of dalargin (SEQ ID NO: 74, Y-(D)-AGFLR) via an N-term linker of peptide vector SEQ ID NO: 48 made it possible to obtain the conjugate SEQ ID NO: 72.

Non-vectorised free dalargin (SEQ ID NO: 74) was used as a control for this brain perfusion study.

Thus, the passage in the brain of vectorised dalargin (SEQ ID NO: 72) compared to its non-vectorised free form (SEQ ID NO: 74) is multiplied by a factor of 21.78.

$K_{in}$ of SEQ ID NO: 72=$19.6 \pm 3.9 \times 10^{-4}$ ml/s/g $K_{in}$ of SEQ ID NO: 74=$0.9 \pm 0.1 \times 10^{-4}$ ml/s/g In addition, this type of in situ brain perfusion experiment also makes it possible to establish a distinction between compounds that remain in the cerebral vascular compartment and those having crossed the abluminal endothelial membrane to enter the brain parenchyma. Indeed, the post-perfusion capillary depletion technique makes it possible to measure if the molecule actually crosses the endothelium in order to enter the brain parenchyma. The use of this technique makes it possible to show that specific peptide vectors (or conjugates) tend to accumulate in the brain parenchyma. This technique (Triguero et al., 1990, *J Neurochem.*, 54(6), 1882-8) is used in order to make a distinction between the fraction of vectors (or conjugates) that transited by the endothelium and entered the brain via the extracellular space or brain cells, and the remaining fraction associated with endothelial cells.

Thus, the key steps of the in situ brain perfusion studies in mouse can be summarised as follows for the vectors and conjugates studied:

i) Evaluation of tolerance (non-toxicity) of the vectors and conjugates at the BBB and preservation of the integrity of this physiological barrier.
ii) Study of kinetics and linearity of brain uptake via RMT by LDLR.
iii) Study of brain uptake rate as a function of vector or conjugate concentration ($T_{max}$, $K_m$).
iv) Study of transport mechanisms using substrates that inhibit or modulate LDLR.
v) Distribution in the compartments of the brain: capillary depletion (Triguero et al., 1990, *J Neurochem.*, 54(6), 1882-8).
vi) Evaluation of binding rate of vectors and conjugates with plasma proteins (albumins, etc.) and study of their influence on brain uptake of these molecules.
vii) Intravenous administration and evaluation of tissue distribution (brain and other organs) as a function of time.

In addition, the $K_{in}$ of these various peptides, across the blood-retinal barrier (BRB), were also determined.

$K_{in}$ of SEQ ID NO: 11=$1.2 \pm 0.2 \times 10^{-4}$ ml/s/g $K_{in}$ of SEQ ID NO: 48=$2.4 \pm 0.3 \times 10^{-4}$ ml/s/g $K_{in}$ of SEQ ID NO: 73=$0.0 \pm 0.0 \times 10^{-4}$ ml/s/g $K_{in}$ of SEQ ID NO: 72=$11.5 \pm 3.3 \times 10^{-4}$ ml/s/g $K_{in}$ of SEQ ID NO: 74=$1.8 \pm 0.2 \times 10^{-4}$ ml/s/g Thus, BRB crossing by vectorised dalargin (SEQ ID NO: 72) is multiplied by a factor of 6.39 compared to its non-vectorised free form (SEQ ID NO: 74).

The invention claimed is:

1. A cyclic peptide or pseudo-peptide which binds human low-density lipoprotein receptor (hLDLR), is 5-8 amino acids in length and comprises the following sequence:

X-M-P-R-Y wherein:
M designates methionine;
P designates proline or an analogue thereof;
R designates arginine;
X designates cysteine or an analogue of a cysteine; and
Y is a peptide of 1 to 4 amino acids comprising a cysteine or an analogue of cysteine.

2. The cyclic peptide or pseudo-peptide of claim 1, wherein Y is a peptide of 1 to 4 amino acids comprising a cysteine or penicillamine (Pen), each in either (L) or (D) conformation.

3. The cyclic peptide or pseudo-peptide of claim 2, wherein X is cysteine and Y comprises cysteine in (L) or (D) conformation.

4. The cyclic peptide or pseudo-peptide of claim 1, wherein P is proline, thiazolidine-4-carboxylic acid (Thz) or pipecolic acid (Pip).

5. The cyclic peptide or pseudo-peptide of claim 1, which comprises at least one peptidomimetic bond.

6. The cyclic peptide or pseudo-peptide of claim 1, which comprises at least one amino acid residue in (D) conformation.

7. The cyclic peptide or pseudo-peptide of claim 1, wherein X is a cysteine or penicillamine (Pen) in either (L) or (D) conformation.

8. The cyclic peptide or pseudo-peptide of claim 7, wherein X is a cysteine in either (L) or (D) conformation.

9. The cyclic peptide or pseudo-peptide of claim 1, wherein the cyclic peptide or pseudo-peptide consists of SEQ ID NO: 48.

10. A conjugate comprising a cyclic peptide or pseudo-peptide of claim 1 that is directly or indirectly conjugated to a molecule of interest.

11. The conjugate of claim 10, wherein the molecule of interest is a therapeutic, diagnostic or medical imaging agent, or a molecular probe.

12. The conjugate of claim 11, wherein said molecule of interest is a small chemical molecule, a peptide or polypeptide, a protein, a nucleic acid, a viral genome or a plasmid, a ribozyme, a marker or a tracer.

13. The conjugate of claim 11, wherein said molecule of interest is an antibiotic, anti-viral agent, immunomodulator, anti-neoplastic agent, anti-inflammatory agent, enzyme, hormone, cytokine, apolipoprotein, growth factor, antigen, antibody or fragment thereof, ribonucleic acid or deoxyribonucleic acid.

14. The conjugate of claim 10, wherein the cyclic peptide or pseudo-peptide consists of SEQ ID NO: 48.

* * * * *